(12) United States Patent
Galbierz et al.

(10) Patent No.: US 9,867,601 B2
(45) Date of Patent: Jan. 16, 2018

(54) RETRACTOR/STABILIZER FOR EXCESSIVE AND/OR REDUNDANT TISSUE AND METHOD OF USE

(71) Applicant: GSquared Medical LLC, Brentwood, TN (US)

(72) Inventors: Thomas R. Galbierz, Brentwood, TN (US); Michael A. Galbierz, St. Louis, MO (US); Gregory A. Gapp, Hopkinsville, KY (US)

(73) Assignee: GSquared Medical LLC, Brentwood, TN (US)

( * ) Notice: Subject to any disclaimer, the term of this patent is extended or adjusted under 35 U.S.C. 154(b) by 66 days.

(21) Appl. No.: 14/816,688

(22) Filed: Aug. 3, 2015

(65) Prior Publication Data

US 2015/0335322 A1 Nov. 26, 2015

Related U.S. Application Data

(63) Continuation of application No. PCT/US2014/013563, filed on Jan. 29, 2014.
(Continued)

(51) Int. Cl.
*A61B 17/02* (2006.01)
*A61F 5/37* (2006.01)
(Continued)

(52) U.S. Cl.
CPC .............. *A61B 17/02* (2013.01); *A61B 46/00* (2016.02); *A61F 5/37* (2013.01); *B32B 3/266* (2013.01);
(Continued)

(58) Field of Classification Search
CPC .. A61F 5/03; A61F 5/37; A61F 5/3715; A61F 5/3761; A61F 5/3776; A61B 17/02;
(Continued)

(56) References Cited

U.S. PATENT DOCUMENTS 1,783,512 A 12/1930 Mather
3,522,800 A 8/1970 Lesser
(Continued)

FOREIGN PATENT DOCUMENTS

EP 0081987 B1 9/1985
EP 0051935 B1 11/1986
(Continued)

OTHER PUBLICATIONS

International Search Report of corresponding application PCT/US2014/013563 dated Jun. 25, 2014.
(Continued)

*Primary Examiner* — Keri J Nelson
(74) *Attorney, Agent, or Firm* — Polster, Lieder, Woodruff & Lucchesi, LC

(57) ABSTRACT

A method for retracting/stabilizing excessive and/or redundant tissue or for compressing redundant tissue including adhering a tension member made of a sheet of material having a surface coated with an adhesive which will adhere to the dermis of a patient to a patient. The step of adhering the tension member to the patient includes: adhering a first portion of the tension member to redundant and/or excessive tissue of the patient and adhering a second portion of the tension member to an anchor point on the patient which is spaced from the redundant and/or excessive tissue such that the tension member is adhered to the patient substantially over the entire surface area of the tension member. When the tension member is applied to the patient, the excessive or redundant tissue pulls against the second portion of the tension member thereby placing the tension member in tension.

24 Claims, 16 Drawing Sheets

Related U.S. Application Data

(60) Provisional application No. 61/866,688, filed on Aug. 16, 2013, provisional application No. 61/760,251, filed on Feb. 4, 2013.

(51) Int. Cl.
  B32B 3/26 (2006.01)
  B32B 7/12 (2006.01)
  A61B 46/00 (2016.01)
  *A61B 17/00* (2006.01)
  *A61B 90/00* (2016.01)
  *A61B 46/20* (2016.01)

(52) U.S. Cl.
  CPC ...... *B32B 7/12* (2013.01); *A61B 2017/00084* (2013.01); *A61B 2017/00893* (2013.01); *A61B 2017/00907* (2013.01); *A61B 2017/00951* (2013.01); *A61B 2046/205* (2016.02); *A61B 2090/037* (2016.02); *B32B 2250/02* (2013.01); *B32B 2307/724* (2013.01); *B32B 2307/7242* (2013.01); *B32B 2519/00* (2013.01)

(58) Field of Classification Search
  CPC ...... A61B 17/0281; A61B 2017/00951; A61B 46/00; A61B 46/20; A61B 46/30; A61B 46/40; A61B 2046/205; B32B 7/12
  USPC ......... 128/845, 846, 849, 851; 600/201, 206
  See application file for complete search history.

(56) References Cited

U.S. PATENT DOCUMENTS

| | | | |
|---|---|---|---|
| 3,826,253 A * | 7/1974 | Larsh | A61B 46/00 128/854 |
| 3,859,157 A | 1/1975 | Morgan | |
| 4,169,472 A * | 10/1979 | Morris | A61B 46/23 128/854 |
| 4,196,723 A * | 4/1980 | Moose, Jr. | A61B 46/00 128/854 |
| 4,432,347 A | 2/1984 | Clavin | |
| 4,619,253 A | 10/1986 | Anhäuser et al. | |
| 4,621,619 A | 11/1986 | Sharpe | |
| 4,825,866 A * | 5/1989 | Pierce | A61B 17/085 606/216 |
| 4,995,383 A * | 2/1991 | Andersson | A61F 13/143 602/19 |
| 5,234,462 A * | 8/1993 | Pavletic | A61B 17/085 606/215 |
| 5,259,835 A | 11/1993 | Clark et al. | |
| 5,275,177 A * | 1/1994 | Wilk | A61M 25/002 128/849 |
| 5,516,581 A | 5/1996 | Kreckel et al. | |
| 5,599,289 A | 2/1997 | Castellana | |
| 5,672,402 A | 9/1997 | Kreckel et al. | |
| 5,985,395 A * | 11/1999 | Comstock | A61B 46/00 128/855 |
| 6,200,195 B1 | 3/2001 | Furuno et al. | |
| 6,350,175 B2 | 2/2002 | Johnson et al. | |
| 6,383,502 B1 | 5/2002 | Dunshee et al. | |
| 6,857,935 B1 | 2/2005 | Dohan | |
| 7,066,182 B2 | 6/2006 | Dunshee | |
| 7,122,236 B2 | 10/2006 | Mitchell et al. | |
| 7,374,633 B2 | 5/2008 | Sellars | |
| 7,473,158 B2 | 1/2009 | Horton | |
| 7,637,798 B2 | 12/2009 | Lutzi | |
| 7,938,121 B2 * | 5/2011 | McKnight | A61F 5/3776 128/845 |
| 9,408,741 B2 * | 8/2016 | Blurton | A61B 17/02 |
| 2002/0191331 A1 * | 12/2002 | Nonaka | B32B 5/20 360/99.19 |
| 2005/0150503 A1 | 7/2005 | Votel | |
| 2008/0210223 A1 | 9/2008 | Joines et al. | |
| 2009/0264709 A1 * | 10/2009 | Blurton | A61B 17/02 600/206 |
| 2010/0145155 A1 * | 6/2010 | Sorajja | A61B 17/02 600/235 |
| 2010/0318013 A1 | 12/2010 | Fabo et al. | |
| 2011/0118646 A1 | 5/2011 | Marcoux et al. | |
| 2011/0250375 A1 | 10/2011 | Bries et al. | |
| 2012/0029295 A1 * | 2/2012 | Long Sharps | A61F 5/026 600/206 |
| 2012/0308754 A1 | 12/2012 | Dehlinger et al. | |
| 2012/0312308 A1 | 12/2012 | Allen | |
| 2013/0048203 A1 | 2/2013 | Yau et al. | |
| 2013/0133668 A1 * | 5/2013 | Fisher | A61F 5/03 128/845 |

FOREIGN PATENT DOCUMENTS

| | | |
|---|---|---|
| EP | 0570317 A1 | 5/1993 |
| EP | 0638301 B1 | 7/1994 |
| EP | 0971661 B1 | 7/1997 |
| EP | 0942940 B1 | 12/1997 |
| EP | 0864311 B1 | 9/1998 |
| EP | 1944001 B2 | 1/2008 |
| WO | 2003043822 A1 | 5/2003 |

OTHER PUBLICATIONS

Written Opinion of the International Searching Authority dated Jun. 25, 2014.

* cited by examiner

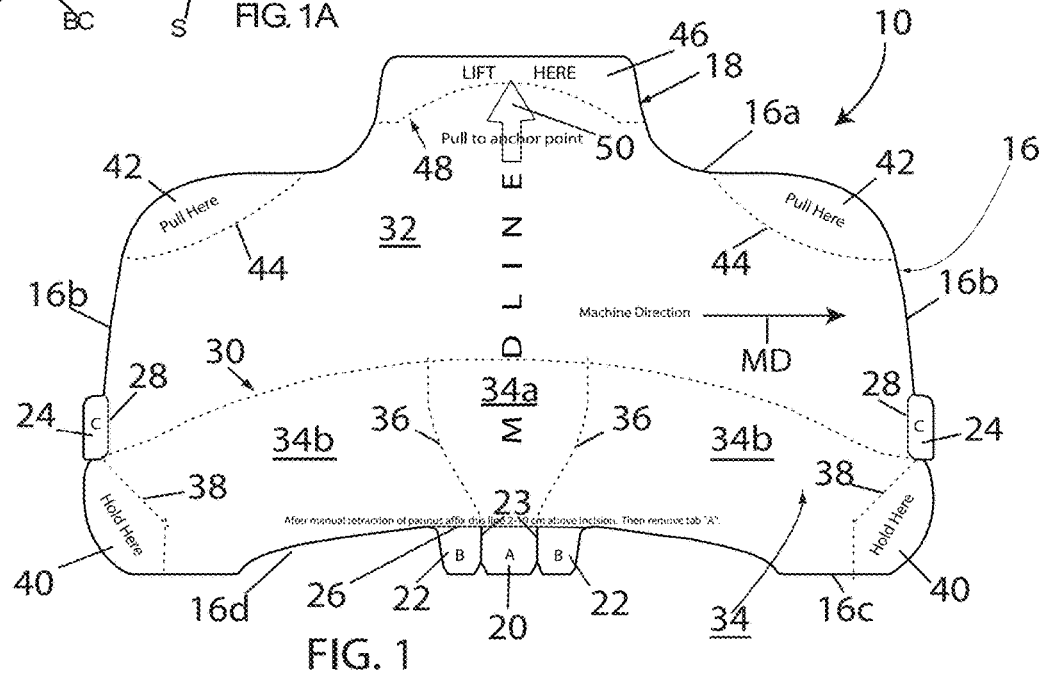
FIG. 1A
FIG. 1
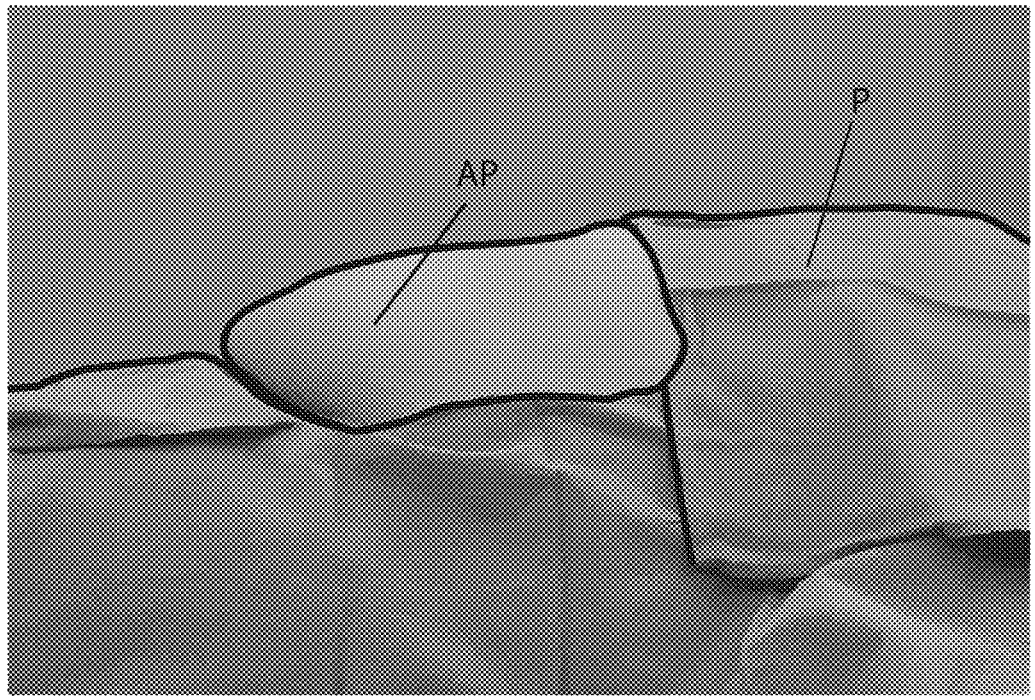
FIG. 2

Manually retract panniculus

Position the retractor 5 cm above incision line

Remove Tab A (Tab A removed)

Apply to patient 2-10 cm above incision line

Remove "B" tabs

Hold in tension as you . . .

Smooth device down onto patient's dermis toward each hip.

Retrofold the device and relax the pannus back to its natural position

Completely remove C panel

Together, in tension, lift and pull retractor cephalad

... and anchor at the xiphoid area

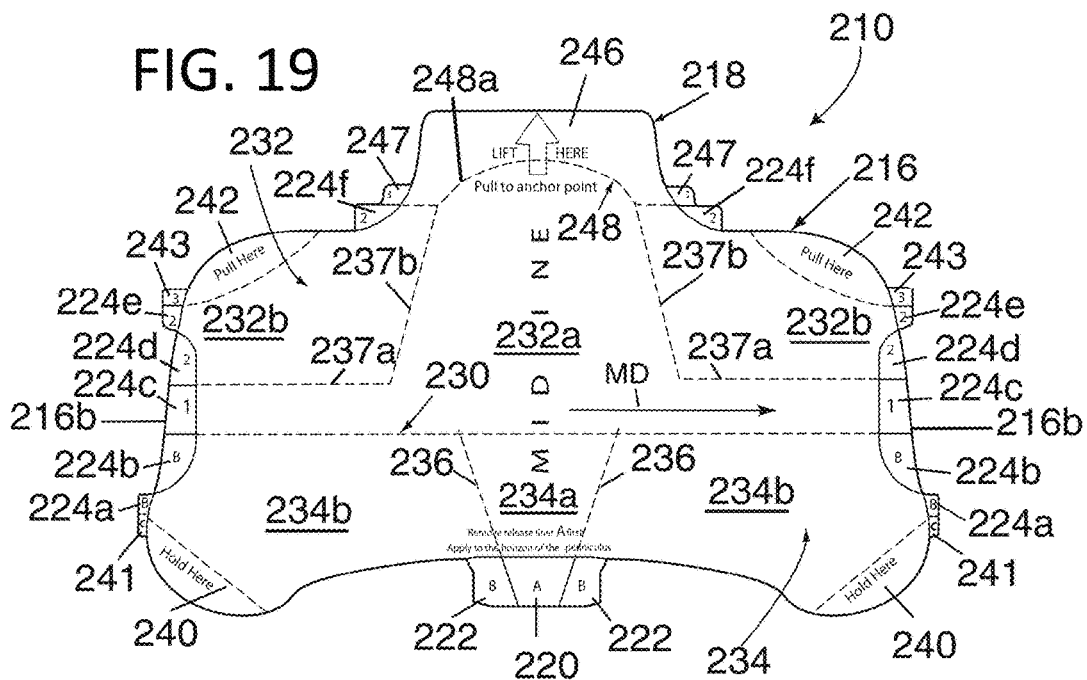

RETRACTOR/STABILIZER FOR EXCESSIVE AND/OR REDUNDANT TISSUE AND METHOD OF USE

CROSS-REFERENCE TO RELATED APPLICATIONS

This application is a continuation of International Application No. PCT/US2014/013563, filed Jan. 29, 2014 which is related to, and claims priority to, U.S. App. No. 61/760,251 filed Feb. 4, 2013 and entitled "Tissue Retraction Device and Method" and U.S. App. No. 61/866,688 filed Aug. 16, 2013 and entitled "Panniculus Retractor/Stabilizer and Method Of Use," all of which are incorporated herein by reference.

STATEMENT REGARDING FEDERALLY SPONSORED RESEARCH OR DEVELOPMENT

Not Applicable.

BACKGROUND OF THE INVENTION

This application relates to a retractor/stabilizer that can be used to displace, retract and/or stabilize excessive and/or redundant tissue (such as adipose tissue, breast tissue, panniculus tissue, etc.) to facilitate access to target sites and/or to facilitate noted medical procedures.

In 2009 the CDC reported that 36.2% of all surgical patients present to the operating room with a BMI (Body Mass Index) over 30. People with a BMI over 30 are considered to be obese, and will commonly have a panniculus (or layer/apron of fat which hangs from the abdomen). Depending on how obese the individual is, the panniculus (or adipose layer or fatty layer) can extend to the pubic hair line (in smaller panniculi) or to the knees and beyond (in very large panniculi). This situation has been arising more frequently in recent years due to people being morbidly obese. Many of these individuals accumulate a large mass of adipose (fatty tissue) in the lower abdominal area producing a panniculus (apron of fat) that hangs, depending on its size, over the groin, genital area and upper thighs.

Patients with such large BMIs require the clinical staff to manage excessive amounts of adipose (or fatty tissue), skin and other tissues (i.e., the panniculus). Currently, those traditional methods are suboptimal. An example of one sub-optimal method is to use silk tape, straps, or athletic tape to retract the panniculus in an opposing or cephalad direction, therefore removing the tissue from the surgical site. Typically, these silk straps or athletic tape are connected or adhered to the operating room table. However, when the panniculus is retracted in this manner, the weight of the panniculus bears down on the patient's diaphragm, making it difficult for anesthesiologists to administer anesthetics and to control the patient's breathing during surgery. The use of adhesive tape results in a lack of sterility in the operating room. Furthermore, the straps or tape may not provide enough friction to hold the apron of fat out of the way and may also not conform to the shape of the panniculus. Additionally, use of the tape can be noisy, and thus disruptive. Also, the nurses' and doctors' gloves can get stuck to the adhesive of the tape while they work to retract the panniculus.

Another method of retracting the panniculus is for two nurses to use a sheet as a sling to pull the abdominal panniculus up and away from the affected area while a third healthcare worker provides care. This can be uncomfortable for the patient and puts two nurses at risk of injury.

Therefore, it is desirable to provide a device to retain the excessive and/or redundant tissue of a patient that holds the excessive and/or redundant tissue out of the way. It is further desirable to provide a device to reposition excessive and/or redundant tissue that is sterile in the surgical field. It is still further desirable to provide a device that is faster to apply, to reposition and hold excessive and/or redundant tissue out of the way. Thus, there is a need in the art to provide a tissue retraction device and method that meets at least one of these desires.

BRIEF SUMMARY OF THE INVENTION

Briefly stated, a multi-ply adhesive device is provided which is formed from a single sheet of at least two-ply material having at least a top layer and a backing layer. One of the top and backing layer has an adhesive applied thereto to adhere the top layer and backing layer together. The adhesive is chosen so that the two layers can be separated, such that one of the layers (i.e., the top layer) can be applied to a desired surface. The top layer can be made from film, cloth, a silicone matting, etc. and preferably has an adhesive coating applied to one surface thereof. The adhesive can be a pressure sensitive adhesive, a silicone adhesive or a co-adhesive. The backing layer covers the adhesive coating, and is removable from the top layer to expose the adhesive coated surface of the top layer so that the top layer can be applied to a surface.

In accordance with one aspect of the device, the device comprises a body portion in which at least of a part of one of the top layer and backing layer is removable to define a removable panel and a tab portion associated with the removable panel. When the removable panel is in the top layer, the top layer of the tab portion is integral with the top layer of body portion and the device includes a cut in the backing layer which separates the backing layer of the tab portion from the backing layer of the body portion. Conversely, when the removable panel is in the backing layer, the backing layer of the tab portion is integral with the backing layer of body portion and the device includes a cut in the top layer which separates the top layer of the tab portion from the top layer of the body portion. The device can be a bandage, a retractor/stabilizer for use during and/or after medical procedures to retract excess and/or redundant tissue from an area of a patient's body, or as a label, sticker, decal and the like.

The tab portion can define an outboard tab which extends from the body portion. In this instance, the cut is formed at an inner edge of the tab portion. Alternatively, the tab portion can define an inboard tab in which an outer edge of the tab portion is generally flush with an outer edge of the body portion. In this instance, the cut defines an inner edge and side edges of the tab portion. The device can be provided with multiple tab portions. The tab portions can all be inboard tab portions, they can all be outboard tab portions, or some tab portions can be inboard tab portions and some tab portions can be outboard tab portions.

In accordance with aspect of the device, the device is a retractor/stabilizer for repositioning and stabilizing excessive and/or redundant tissue. The retractor/stabilizer comprises a top layer and a backing layer, and the top layer has an adhesive applied thereto which is exposed when the backing layer is separated from the top layer to enable the top layer to be applied to a surface (such as a patient's dermis or skin). The bottom edge of the body can define a curvature (which can be concave) that simulates the curvature of a patient's abdomen and/or other anatomy of the patient. The top layer can be made from a flexible or semi-rigid material comprised of one or more of the following: a plastic, a natural cloth/fabric, a man-made cloth/fabric, spandex, a silicone matting, paper, plastic, foam, and film. The top layer is vapor-permeable and breathable, or it can be vapor-impermeable.

The top layer can have a machine direction that runs in a width-wise direction of the retractor/stabilizer or in a top-to-bottom direction of the retractor/stabilizer.

The top layer or the adhesive can contain a pharmaceutical agent that is delivered to the patient's skin when the retractor/stabilizer is applied to a patient.

In accordance with one aspect of the retractor/stabilizer, the retractor/stabilizer comprises a body having a top edge, side edges and a bottom edge; and at least one protected grasping/holding area located at an edge or corner of the retractor/stabilizer; the grasping area being configured to be graspable by a technician without the technician contacting exposed adhesive of the top layer. The grasping area can be integral with the body, in which case it is defined in part by a cut in the backing layer which divides the backing layer of the grasping area from the rest of the backing layer. Alternatively, the protected grasping area can be defined by a portion of the top layer being folded or hemmed such that the top layer adhesive is turned back on itself, face to face, to produce the adhesive-free grasping area. As a further alternative, the protected grasping area can be defined by a separate piece (such as a handle) which is adhered to the retractor/stabilizer body.

The at least one grasping area can comprise a grasping area each corner of the retractor stabilizer. In an illustrative embodiment, the protected grasping areas can be formed by corner cuts formed in the backing layer. Thus, the backing layer at these protected grasping areas will remain with the top layer of the protected grasping areas even after removal of the upper and lower panels from the top layer. This gives the practitioners an area to grasp wherein the adhesive of the top layer is not exposed and which can thus be grasped to manipulate the top layer after removal of the backing layer without the practitioners' gloves coming into contact with, and getting stuck to, the adhesive of the top layer. Alternatively, the grasping area can be defined by a portion of the top layer being folded or hemmed over on itself such that the top layer adhesive is turned back on itself, face to face, to produce the adhesive-free grasping area. As another alternative, the grasping area can be defined by a part that is adhered to the retractor/stabilizer body.

Additionally, the at least one grasping area can include an upper grasping area at the upper edge of the body. This upper grasping area can be positioned at the end of a neck extending from the upper edge of the body. In this instance, the retractor/stabilizer can include a cut in the backing layer in the neck such that a lower portion of the neck backing layer is connected to the upper panel and such that an upper portion of the neck backing layer remains with the neck when the upper panel backing layer is removed to define the upper grasping area.

In accordance with another aspect of the retractor/stabilizer, the retractor/stabilizer includes at least one tab associated with the backing layer and positioned at an edge of the body. The tab is configured and formed such that pulling on the tab in a direction away from the top layer will remove the backing layer from the top layer. The tab can be integral with the body and is defined in part by a cut in the top layer at an inner end of the at least one tab such that the backing layer portion of the tab remains connected to the backing layer of the panel with which the tab is associated, yet the top layer of the tab is separated from the top layer of the body with which the tab is associated.

At least one tab is associated with each of the sections or portions of the backing layer. Thus, there is at least one positioning portion tab associated with the positioning portion of the lower panel, at least one lower panel second portion tab associated with the lower panel second portion, and at least one upper panel tab associated with the upper panel. The tab is operable to remove the backing layer from the top layer of a respective panel without the technician coming into contact with the adhesive coating of the top layer.

In accordance with one aspect of the tab, the tab is integral with the retractor/stabilizer body and is formed such that the backing layer portion of the tab remains connected to the backing layer of the panel with which the tab is associated, yet the top layer of the tab is separated from the top layer of the panel with which the tab is associated. Thus, when the tab is pulled away from the panel, the tab will pull the backing layer away from the top layer, and the top layer of the tab will remain with the backing layer of the tab. To this end, a cut is formed in the top layer to define an edge of the tab such that pulling a selected tab in a direction away from the top layer will remove the backing layer section associated with the tab of the top layer. This cut in the top layer ensures that the top layer of the tab remains with the backing layer of the tab. This eliminates the need for weeding, folding, bending or crack back to operate the tabs thereby making use of the retractor/stabilizer easier. Further, because the top layer remains with the backing layer in the tab, the possibility of the practitioners' gloves from coming into contact with, and getting stuck to, the adhesive of the top layer is reduced.

In another variation of the tab, the tab can be defined by a tab member which is separate from the assembly from which the retractor/stabilizer is formed, and which is adhered to the backing layer of each panel portion.

To facilitate placement of the retractor/stabilizer top layer on a patient, the retractor/stabilizer can be provided with a back cut in the backing layer extending from one side of the backing layer to the other side of the backing layer, to separate the backing layer into an upper panel and a lower panel. In this instance, the at least one tab comprises at least one upper panel tab associated with the backing layer upper panel and at least one lower panel tab associated with the backing layer lower panel. The side-to-side back cut can define a curvature (which can be concave) that simulates the curvature of a patient's abdomen and/or other anatomy of the patient.

The retractor/stabilizer can further comprise a first lower panel back cut in the backing layer lower panel extending from the bottom edge to a point proximate the side-to-side back cut to divide the lower panel in to at least a lower panel positioning portion and a lower panel second portion. A positioning portion tab is associated with the lower panel positioning portion, and a lower panel second portion tab associated with the lower panel second portion. The two noted tabs are defined by a cut in the top layer of the body at an inner end of the respective tab such that pulling on the respective tab in a direction away from the top layer will remove the respective panel portion from the top layer.

The backing layer lower panel positioning portion can define a central portion of the backing lower panel. In this instance, the backing layer lower panel second portion defines a first side portion of the lower panel on a first side of the central portion. The backing layer lower panel also includes third lower panel portion on a side of the positioning portion opposite of the lower panel second portion. A third portion tab is associated with the backing layer lower panel third portion and is defined by a cut in the top layer at an inner end of the lower panel third portion tab such that pulling on the lower panel third portion tab in a direction away from the top layer will remove the backing layer lower panel third portion from the top layer.

The tabs for the backing layer lower panel portions can be outboard tabs which extend from the bottom edge of the body. Alternatively, the backing layer lower panel portion tabs can be inboard tabs which have an outer edge that is generally flush with the edge of the body at which the tab is located. Further, the backing layer lower panel portion tabs can include both inboard and outboard tabs.

The at least one upper panel tab can be located at one or both of the side edge and upper edge of the body. The at least one upper panel tab can includes a first upper panel tab located at the side edge and a second upper panel tab positioned at the upper edge of the body.

The backing layer upper panel can include a first lower portion and at least one upper portion. In this instance, each of the upper panel portions will have associated tabs to facilitate removal of the respective backing panel upper portion from the top layer. The body will thus include a cut in the top layer at an inner end of each of the upper panel portion tabs such that pulling on the tabs in a direction away from the top layer will remove the respective upper panel portion from the top layer. The backing layer upper panel can include two upper portions, each of which have associated tabs to facilitate removal of the respective backing panel upper portion from the top layer.

The top layer of the retractor/stabilizer can be provided with a removable panel which is defined at least in part by a tear line in the top layer. In one aspect, the tear line can be a cut line which is spaced from all edges of the top layer and define all edges of the panel, such that the removable panel is separated from the remainder of the top layer when the backing layer is removed from the top layer.

In an alternate embodiment of the removable panel, the tear line is at least in part is a perforated face cut. In one variation of this embodiment, the removable panel is located at an edge of said top layer. In this instance, the retractor/stabilizer includes at least one tab associated with the removable panel of the top layer and which is defined at least in part by a cut in the backing layer such that the backing layer of the removable panel tab remains with the top layer of the removable panel tab and pulling on the removable panel tab in a direction away from a surface (such as a patient's skin/dermis) to which the retractor/stabilizer top layer is applied will separate the removable panel of the top layer from the remainder of the top layer. In one variation of this embodiment, the removable panel tab is located at an edge of the top layer. In another variation, the removable panel tab is spaced from an edge of the top layer and the tear line extends from an edge of the top layer to the removable panel tab.

In another embodiment of the removable panel, the removable panel is spaced from the edges of the top layer. In this embodiment, the retractor/stabilizer comprises a removable panel tab associated with the removable panel. The removable panel tab being defined at least in part by a cut in the backing layer at an inner end of the removable panel tab such that the backing layer of the removable panel tab remains with the top layer of the removable panel tab and pulling on the removable panel tab in a direction away from the surface to which the top layer is applied will separate the removable panel of the top layer from the remainder of the top layer. The removable panel can be hingedly connected to the top layer, such that the removable panel defines an openable and closeable window; the tear line extending from opposite sides of the removable panel tab. Alternatively, the tear line can be a continuous tear line having two ends, each of which are at the removable panel tab, such that the removable panel separates completely from the top layer when the removable panel tab is pulled away from the surface to which the retractor/stabilizer is applied.

The tear line for the removable panel can define an arc. In the instance where the top layer has a machine direction, the spacing between perforations of the tear line and the size of the perforations of the tear line vary based on the angle of the perforated line relative to the machine direction. In particular, when the tear line is generally parallel to the machine direction, the perforations are defined by microcuts or dots, and the perforations of the tear line increase in length and the distance between perforations decreases as the angle defined by the tear line and the machine direction increases.

In accordance with another aspect, the retractor/stabilizer can be provided with a tear strip defined by a pair of spaced apart tears lines in top layer. These tear strip tear lines each are defined by perforated face cuts. The tear strip extends from a first edge of the top layer to an opposite edge of the top layer; whereby removal of the tear strip separates the top layer into two pieces. A tear strip tab can be provided for the tear strip. The tear strip tab is positioned at an edge of the top layer and is defined in part by a cut in the backing layer such that the backing layer of the tab remains with the top layer of the tab when the tab is grasped and pulled.

In accordance with another aspect, an extension member can be provided to effectively increase the length of the retractor/stabilizer. The extension member disclosed can be used, for example, with for patients having very large BMIs (i.e., above 45).

The extension member, like the retractor/stabilizer body, comprises a backing layer and a top layer with an adhesive applied to the top layer. The adhesive is exposed when the extension member backing layer is separated from the top layer to enable the extension member top layer to be applied to a surface. The top layer of the extension member and the top layer of the retractor/stabilizer body are adapted to be adhered together to thus define a unitary member. The extension member top layer has a machine direction which, preferably, runs in a top-to-bottom direction of the extension member.

The extension member comprises a top edge, a bottom edge, and side edges. A cross-wise extending back cut extends from one side edge to the opposite side edge of the extension member to divide the extension member backing layer into an upper panel and a lower panel. At least one upper panel tab associated with the backing layer upper panel and at least one lower panel tab associated with the lower panel. The tabs are configured such that pulling on a respective tab in a direction away from the top layer will remove the associated baking layer panel from the top layer. Additionally, the extension member can be provided with protected grasping areas at corners of the extension member.

The upper panel tabs and the lower panel tabs of the extension member can be positioned along at least one of the side edges of the extension member. Further, the extension member tabs can be are outboard tabs which extend from the at least one side edge, or they can be inboard tabs.

The body of the retractor/stabilizer and the extension member have been described to include several variations, including various tab configuration, tear lines, various removable panels, etc. The various tab configurations, panel configurations, and tab configurations can be combined as may be desired. Thus, for example, the tab configuration of one embodiment cab be applied to a different embodiment.

A method for using the retractor/stabilizer to retract/stabilize excessive and/or redundant tissue or for compressing redundant tissue is also disclosed. The method comprises adhering a tension member (such as the top layer of the retractor/stabilizer) to the patient. The tension member comprises a sheet of material having a surface coated with an adhesive which will adhere to the dermis of a patient. The tension member is applied to the patient by adhering a first portion of the tension member to redundant and/or excessive tissue of the patient; and adhering a second portion of the tension member to an anchor point on the patient which is spaced from the redundant and/or excessive tissue. When the tension member is applied, the excessive or redundant tissue pulls against the second portion of the tension member thereby placing the tension member in tension. Preferably, the tension member is self-contained, and is secured only to the patient. Stated differently use of the tension member does not require any device external of the patient, other than the retractor/stabilizer itself. Thus, for example, the tension member need not be adhered to a bed or table on which the patient is laying. When applied to the patient, the tension member conforms to the shape of the patient and supports the excessive and/or redundant tissue after application.

In one aspect of the method, the tension member comprises a top layer of a retractor/stabilizer which also comprises a backing layer and an adhesive applied to the top layer. At least one protective grasping area is located at an edge or corner of the retractor/stabilizer which has a substantially adhesive free surface when the backing layer is removed from the retractor/stabilizer. Additionally at least one tab is associated with the backing layer, the tab being configured such that pulling on the tab in a direction away from the top layer will remove the backing layer from the top layer. With this retractor/stabilizer, the method comprises while holding onto the grasping area, grabbing the at least one tab and pulling the at least one tab away from the top layer to remove the bottom layer from the top layer to expose the adhesive of the top layer at substantially all portions of the top layer. Then, a lower portion of the top layer is adhered to the excessive and/or redundant tissue of the patient and the upper end of the top layer is adhered to at least one anchor point on the patient. The top layer can be secured first to the excessive and/or redundant tissue, in which case, the method comprises pulling the top layer towards the anchor point after the top layer has been adhered to the excessive and/or redundant tissue and then securing the upper end of the top layer to the at least one anchor point. Alternatively, the top layer can be secured first to the at least one anchor point, in which case, the method comprises pulling the top layer towards the excessive and/or redundant tissue after the top layer has been adhered to the anchor point and then securing the lower end of the top layer to the excessive and/or redundant tissue.

As part of the procedure of applying the retractor/stabilizer to the patient, the method includes a step of retracting the excessive and/or redundant tissue prior to adhering the lower portion of the top layer to the radius of the excessive and/or redundant tissue. This retraction step can be performed manually or carried out by machine (or by robot).

The excessive and/or redundant tissue is allowed to relax after the lower portion of the top layer has been adhered to the radius of the excessive and/or redundant tissue and before the pulling step.

In the embodiment of the retractor/stabilizer wherein the backing layer is divided into an upper panel and a lower panel, and the stabilizer/retractor is provided with a tab associated with each panel, the step of applying the top layer to the excessive and/or redundant tissue comprising removing the lower panel of the backing layer to expose the adhesive in a lower portion of the top layer. Similarly, the step of applying the top layer to the anchor point comprises removing the upper panel of the backing to expose the adhesive in an upper portion of the top layer.

In the embodiment of the retractor/stabilizer wherein the lower panel of the backing layer is divided in to a positioning portion and at least one second portion, the step of removing the lower panel of the backing layer comprises removing the positioning portion of the backing layer from the top layer to expose a positioning portion in the lower portion of the top layer, adhering the positioning portion of the lower portion of the top layer to the excessive and/or redundant tissue; removing a remainder of the lower portion of the backing layer to expose the adhesive in the remainder of the lower portion of the top layer (except for in the grasping areas); and adhering the remainder of the lower portion of the top layer to the excessive and/or redundant tissue.

In accordance with one aspect of the method, the retractor/stabilizer can be removed from the patient upon completion of the procedure. In accordance with another aspect of the method, the retractor/stabilizer can remain on the patient long term to facilitate healing of an incision, a wound, or an infection which would otherwise be covered by the patient's excessive and/or redundant tissue.

In the instance wherein the excessive and/or redundant tissue is a panniculus, the first portion of the tension member is applied to the excessive and/or redundant tissue to encasing the radius of the panniculus. In this instance, the anchor point is preferably the xiphoid area of the patient.

In the instance wherein the excessive and/or redundant tissue is located at a hip area of the patient, and the at least one anchor point is the front and/or back of the patient.

In the instance wherein the excessive and/or redundant tissue is located on the back of the patient; and the anchor point is on the patient's back spaced axially from the excessive and/or redundant tissue.

In the instance wherein the excessive and/or redundant tissue is breast tissue; and the anchor point is a shoulder or side area of the patient.

The steps of retracting, repositioning, and stabilizing excessive and/or redundant tissue as noted above can be used to facilitate numerous medical procedures.

For example, application of the retractor/stabilizer can be used to improve and/or at a minimum does not restrict diaphragmatic excursion. In accordance with this aspect of the method, the retractor/stabilizer anchors the excessive and/or redundant tissue of the patient to the xiphoid area of the patient. Once the excessive and/or redundant tissue is anchored, the dermis is allowed to relax. In accordance with this method, the excessive and/or redundant tissue can be the abdomen of a pregnant woman undergoing a caesarian section operation or the panniculus of an obese person.

When the medical procedure is an imaging procedure; the method can further comprise removing a predefined panel from the top layer to expose the patient's dermis. In accordance with an embodiment of the retractor/stabilizer, the predefined panel is removed from the top layer after the top layer has been adhered to the patient. In accordance with a variation of the removable panel, the panel can be reapplied to the patient once the imaging procedure has been completed.

In accordance with another aspect of the retractor/stabilizer, use of the retractor/stabilizer will reduce the distance through the tissue to the target site minimizing and reducing the distance between the dermis and the target area.

In another aspect, use of the retractor/stabilizer can prevent chest wall compression and diaphragm restriction during a surgical procedure. In accordance with this aspect, a tension member comprising a sheet of material having a surface coated with an adhesive which will adhere to the dermis of a patient is adhered to the patient. The step of adhering the tension member to the patient includes adhering a first portion of the tension member to the patient in an area proximate the patient's diaphragm and adhering a second portion of the tension member to the patient in an area proximate the patient's xiphoid process and upper chest wall; and adhering a third portion of the tension member which is remote from the first and second portions to the patient in the patient's abdominal region such that the third portion is adhered to redundant and/or excessive tissue of the patient on or about the abdominal region, whereby the excessive or redundant tissue pulls against the first and second portions of the tension member thereby placing the tension member in tension.

The stabilizer/retractors disclosed and described below can be used with virtually any procedure in which excessive and/or redundant tissue must be moved to enable access to a surgical or wound site. Such procedures include mapping, electrode placement, monitoring, fetal ultrasound or sonography, laparotomies (C-sections, total abdominal hysterectomies, hernias, bowel resections, etc.), incision/wound care, vascular access (e.g., to the femoral artery in the area of the groin), access for nerve block and similar techniques used during anesthesiology and/or for pain management, radiology/oncology, orthopedic and neurological procedures (e.g., spinal taps), plastic surgery (i.e., breast tissue management), ENT procedures, and trauma procedures. Various other embodiments of the retractor/stabilizer are disclosed which facilitate retraction/stabilization of excessive and/or redundant tissue for various of these procedures.

BRIEF DESCRIPTION OF THE SEVERAL VIEWS OF THE DRAWINGS

FIG. 1 is a plan view of a first embodiment of a retractor/stabilizer for excessive and/or redundant tissue;

FIG. 1A is a cross-sectional schematic view of the retractor/stabilizer to show the two layers of the retractor/stabilizer, as provided;

FIG. 2 is a photograph of a patient prior to application of the retractor/stabilizer;

FIG. 19 is a plan view of a third embodiment of the retractor/stabilizer;

FIG. 20 is a plan view of a variation of the retractor/stabilizer of FIG. 1 wherein the retractor/stabilizer is modified to make a section of the top layer removable.

Corresponding reference numerals will be used throughout the several figures of the drawings.

DETAILED DESCRIPTION OF THE INVENTION

Figure 3:
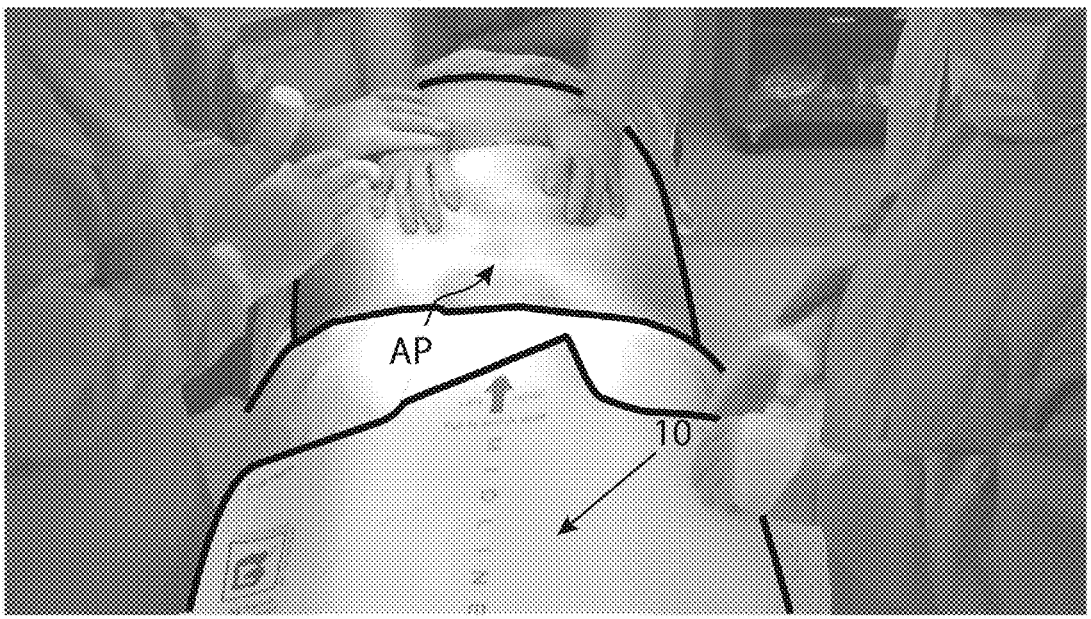
FIG. 3 is a photograph showing medical practitioners manually retracting the patient's panniculus in preparation for application of the retractor/stabilizer.

The following detailed description illustrates the invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

A first embodiment of a retractor/stabilizer 10 is shown in plan view in FIG. 1, and in enlarged cross-section in FIG. 1A. Common to all the embodiments is the fact that the retractor/stabilizer is formed (such as by die cutting) of a multi-ply sheet assembly comprised of a backing layer, release layer or liner 12 to which a top layer 14 is adhered by means of an adhesive A on a surface of the top layer. The top layer can have several properties/characteristics:

- The top layer can be made from a film, cloth/fabric (formed from either natural or man-made materials), spandex, a silicone matting, paper, plastic, foam, plastic, compounds/composites, or any other desired material which will work suitably as described below.
- The top layer can be single ply or multi-ply.
- The top layer can be a woven or nonwoven mesh or it can be solid or continuous.
- The top layer can be breathable (vapor permeable) or vapor impermeable.
- The top layer can be made from a material which can be incised (i.e., cut or sliced), punctured, perforated or penetrated with an instrument or device after the top layer has been applied to the patient. Incising of the top layer after application to the patient may be necessary depending on the proximity of the retractor/stabilizer to the incision area.
- The top layer can be transparent, translucent or opaque.
- The adhesive is typically a pressure-sensitive adhesive (PSA), but can be an acrylate adhesive, a silicone adhesive or a co-adhesive.
- The top layer can be provided with reinforcing sections or strips made of either the same material as the top layer or from a different material. These reinforcing sections or strips can be applied to the top layer of the retractor/stabilizer. Alternatively, the top layer of the retractor/stabilizer can have reinforcing threads or fibers incorporated into it. These reinforcing threads or fibers can be parallel to the machine direction of the top layer, perpendicular to the machine direction of the top layer, or at an angle (other than about 0° or about) 90° to the machine direction of the top layer. As another alternative, such reinforcing threads or fibers need not be parallel to each other, and can form random configurations (be spaghetti-like) in the top layer.
- A portion (or all of) the top layer and/or adhesive layer can be impregnated or infused with a pharmaceutical agent for delivery of the agent to the patient, such that the retractor/stabilizer functions as a transdermal delivery device for treatment of a wound, patient or both.
- The retractor/stabilizer top layer can include an indicator to show evidence of a biological, temperature, chemical, vapor or gas in concentrations, rates or values.

Various of the combinations of top layer and adhesive would allow for the retractor/stabilizer to be autoclaved and reused. Preferably, the film/top layer is latex free. An anti-static coating can be applied to the top layer if desired. An anti-static ingredient can also be included with the adhesive. Further, the top layer can be provided with antimicrobial/antibacterial agents, which can, for example, be mixed in with or applied to the surface of the adhesive, such that the antimicrobial/antibacterial agents are in contact with the patient's skin during use. The retractor/stabilizer is preferably sterilized, such as by gamma radiation, and is sterilizable.

In one illustrative embodiment, the retractor/stabilizer can be made from a product such as 3M 9865 medical grade tape (available from 3M) or MACTac TM1030 (available from MACtac North America, of Stow, Ohio, US). In the 3M medical tape the release layer (or backing layer) is currently comprised of 63 lb. poly-coated Kraft paper with a thin (4.9 mils/0.12 mm) silicone coating S on one side of the backing paper and a 3.0 mil (0.08 mm) translucent polyethylene film top layer with an adhesive coating A applied to one side of the top layer. The adhesive is an acrylate adhesive which is designed for medical/surgical use. As can be appreciated, the top layer is applied to the Kraft paper liner with the adhesive side of the top layer in contact with the silicone coated side of the paper liner. When the liner is removed from the top layer, the adhesive side of the top layer will be exposed for application of the top layer to a desired surface (such as a patient's body).

To enable use of the retractor/stabilizer, a series of cuts are formed in the blank from which the retractor/stabilizer is formed to facilitate removal of the backing layer from the top layer. FIG. 1A shows that some cuts are top or face cuts FC which extend just through the top layer 14 (but not through the backing layer 12), and that other cuts are back cuts BC which extend just through the backing layer 12, but not through the top layer 14. Back cuts are used to form integral protected grasping areas at "corners" of the retractor/stabilizer. The back cuts BC which form or define the grasp areas allow for the backing layer 12 to remain with the top layer 14 in these areas. This allows for medical personnel to hold and position the retractor/stabilizer when a portion, or all, of the backing layer 12 (except for the backing layer in the protected grasping areas) has been removed from the top layer without having their gloves contact the adhesive.

Back cuts can also be formed to divide the backing layer into discrete sections or panels which can be removed independently of each other.

To facilitate removal of the back layer, each panel can be provided with at least one tab. The tab enables the technician to remove the backing layer from the top layer of the retractor/stabilizer without coming into contact with the adhesive of the top layer. In a first embodiment of the tabs, the tabs are formed from the sheet from which the retractor/stabilizer is formed. That is, the tabs are integral with the body of the retractor/stabilizer. To this end, the tabs can be defined by face slices or cuts FC at an upper or inner end of each tab. These face cuts cause the top layer 14 to remain with the backing layer 12 in the area of the tab. Thus, the medical personnel can simply grasp a tab and pull downwardly to separate the backing layer 12 (or portion of the backing layer) from the top layer 14. These tabs allow for the practitioner to remove the backing layer without his or her gloves contacting the adhesive of the top layer. In another embodiment of the tabs, the tabs are formed separately from the retractor/stabilizer body (i.e., is not integral with the retractor/stabilizer) and are adhered to the backing layer of the retractor/stabilizer.

Unless otherwise noted, the various slices or cuts are all through cuts. That is, the back cuts extend through the backing layer (but not through the top layer) and the face cuts extend through the top layer (but not through the backing layer). Full cuts, which extend through both the top layer and the backing layer are noted in certain circumstances. Thus, there is no weeding, folding, bending or crack back needed to operate the tabs and/or remove the backing layer.

The retractor/stabilizer is initially described for use in retracting and stabilizing the pannus or panniculus of a patient. However, the stabilizer/retractors disclosed and described below can be used with virtually any procedure in which excessive and/or redundant tissue must be moved to enable access to the procedural/target site. Such procedures include, in addition to retraction of the pannus, mapping, electrode placement, monitoring, fetal ultrasound or sonography, laparotomies (C-sections, total abdominal hysterectomies, hernias, bowel resections, etc.), incision/wound care, vascular access (e.g., to the femoral artery in the area of the groin), access for nerve block and similar techniques used during anesthesiology and/or for pain management, radiology/oncology, orthopedic and neurological procedures (e.g., spinal taps), plastic surgery (i.e., breast tissue management), ENT procedures and trauma procedures.

Turning to FIG. 1, a retractor/stabilizer 10 has a generally quadrilaterally shaped body 16 having an upper edge 16a, side edges 16b, and a lower edge 16c. The lower edge 16c is cut to define a concave arc section 16d. This curved shape is preferred because it better fits the patient's anatomy (i.e., the contour of the abdomen where the device is applied to a panniculus) when in use. Stated differently, the curved section 16d of the lower edge 16c defines a concave radius or curvature that simulates or represents the curvature of patient's abdomen. However, it will be appreciated that the lower edge could be generally straight or even convexly curved if desired. The retractor/stabilizer also includes a tongue 18 extending generally from the center of the upper edge 16a. When corners of the release liner are sharp (i.e., right angled), there is a tendency for the top layer to lift off the patient's skin due to the concentration of stresses and forces at the right-angle corner. Thus, the corners of the retractor/stabilizer 10 are shown to be radiused. However, the corners could be sharp corners, if desired.

A first tab 20, labeled "A" in the drawings, extends from the center of the bottom curved edge 16d. Two tabs 22, labeled "B" in the drawings, are formed on opposite sides of the A-tab 20, and likewise extend from the bottom curved edge 16d. The B-tabs 22 are shown to be adjacent the A-tab 20, but could be spaced from the A-tab, anywhere along the bottom edge 16c,d of the retractor/stabilizer body portion 16. Side tabs 24, labeled "C" in the drawings, are formed above the bottom right and left corners of the retractor/stabilizer 10 and extend from the side edges 16b. However, as seen, the outer edges of the C-tabs 24 are essentially even with the upper edge of the lower corners of the retractor/stabilizer. Although near the bottom of the retractor/stabilizer, the side C-tabs 24 could be formed at any desired point along the side edges 16b of the retractor/stabilizer body portion 16. As seen, the B-tabs 22 are adjacent the A-tab 20, and thus a single face cut 26 extends across a top of the three tabs. The A and B-tabs are separated from each other by full cuts 23 which extend through both the top layer 14 and backing layer 12, so that the tabs are fully independent of each other. Face cuts 28 extend generally parallel to the side edges 16b of the retractor/stabilizer body 16 along an inner end of the side C-tabs 24.

An upwardly curved back cut 30 typically extends from one side edge 16b to the other side edge 16b to divide the backing layer 12 into an upper panel 32 and a lower panel 34. This back cut 30, like the curved section 16d of the lower edge 16c, defines a concave radius or curvature that simulates or represents the curvature of patient's abdomen. However, the back cut 30 need not be parallel to the curved edge 16d of the retractor/stabilizer. As shown, the backing layer lower panel 34 comprises about the lower one-third of the body 16. A back cut 36 extends upwardly from each corner of the A-tab 20 to the back cut 30. The back cuts 36 divide the backing lower panel 34 into a central alignment portion 34a, which is used to orient and anchor the retractor/stabilizer on the patient, and side portions 34b which encase the radius of the excessive and/or redundant tissue (e.g., the panniculus in FIGS. 4-15) and further anchors the device to the patient's dermis. The two back cuts 36, which define the lower panel central portion 34a curve upwardly and outwardly, giving the central portion 34a the shape, in general, of an inverted bottle. As seen, the A-tab 20 is connected to the central portion 34a and a B-tab 22 is connected to each of the side portions 34b. As will be described below, this construction allows for the three sub-panels 34a and 34b to be removed from the top layer independently of each other, and allows for the practitioner to expose only a portion of the adhesive of the top layer, thereby making application of the retractor/stabilizer to a patient's skin somewhat easier. As will become apparent below, the sub-panel 34a is the first panel from which the backing layer is removed, and is used to align the retractor/stabilizer on the patient. As such, it is the initial anchor point of the retractor/stabilizer on the patient and assists in the removal of the backing layer from the other panels (i.e., panels 34b and 32).

Back cuts 38 are made inwardly of the lower corners of the body 16 in the lower panel 34 to define lower grasping areas 40. Upper grasping areas 42 are defined by back cuts 44 at the upper corners of the body upper panel 32. Lastly, a grasping area 46 is formed on the neck 18 by a back cut 48. The cuts 38, 44 and 48 enable the backing layer 12 to remain with the top layer 14 in each of the grasping areas 40, 42 and 46. As will become apparent below, this will form an area in which the adhesive remains covered during application of the retractor/stabilizer 10 which the medical practitioner can hold on to the stabilizer at the grasping areas without fear of his/her gloves becoming stuck to the top layer 14. The back cuts 38 for the lower grasping areas 40 are typically defined by a pair of intersecting straight cuts; and the cuts 44 for the upper grasping areas 42 are inwardly curving. The actual shape of the cut (and thus of the grasping area) is not important, and the grasping areas can be any desired shape, as long as they are large enough for a practitioner to hold onto during application (and removal) of the retractor/stabilizer without worrying about getting his/her gloves stuck to the adhesive of the top layer. The back cut 48 for the grasping area 46 of the tongue 18 is shown to have first portions extending inwardly from the side edges of the tongue which are joined by an upwardly directed arc. Again, this cut can be of generally any desired shape, as long as the grasping area 48 for the tongue 18 is large enough for the practitioner to grasp hold of the tongue during use of the retractor/stabilizer without getting his/her gloves stuck to the adhesive side of the top layer.

Although the grasping areas 40, 42 and 46 are described as being defined by back cuts and thus as being integral with the retractor/stabilizer, they could be formed by separate grasps or handles which are adhered to the top layer. These grasping areas or handles would accomplish the same function as the grasping areas which are integral with the retractor/stabilizer—they would allow for the technician to hold the top layer of the retractor/stabilizer without contacting the adhesive of the top layer after the backing layer has been removed.

Although the tabs and grasping areas are described as being graspable by practitioners (i.e., humans), the tabs and grasping areas could be designed to be grasped by robotic equipment (such as the da Vinci® robotic surgical system), to enable the retractor to be applied robotically.

Lastly, the retractor/stabilizer 10 can be provided with instructional indicial. Thus, the lower grasping areas 40 are each shown to be printed with the phrase "Hold Here"; the upper grasping areas 42 are each printed with the phrase "Pull Here"; and the tongue grasping area 46 is printed with the phrase "Lift Here". The central portion 34a of the lower panel is printed with the phrase "Remove release liner A first", "After manual retraction of the panniculus, remove Tab A", or the like. An instructional phrase "Apply to the horizon of the panniculus" or "Apply this line 5 cm above the incision" or the like can be printed across the center of the lower panel 34. The upper panel 32 has the phrase "Pull to anchor point" printed in the bottom of the tongue 18. Additionally, an arrow 50 is printed at the junction between the body and the neck which points toward the neck, and in a cephalad direction during use. Finally, the word "MIDLINE" extends along the center top-to-bottom axis of the retractor/stabilizer. This MIDLINE notation shows where the side-to-side center (or vertical axis) of the retractor/stabilizer is located. In fact, the retractor/stabilizer 10 is symmetrical about its vertical axis.

Turning to FIGS. 2-16, the use of the retractor/stabilizer will be described in conjunction with the retraction/stabilization of a patient's panniculus. Initially, FIG. 2 shows a portion of patient P with an abdominal panniculus AP exposed. The remainder of the patient's body is draped. At this point, the patient is in a supine position.

Figure 4:
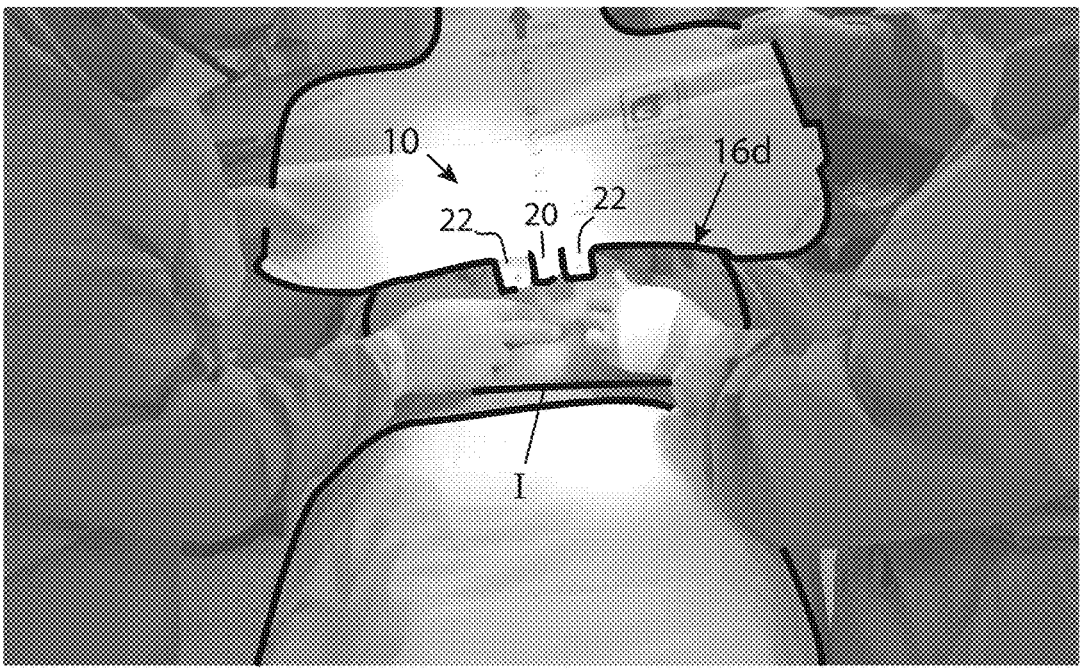
FIG. 4 is a photograph showing medical practitioners positioning the retractor/stabilizer to apply it to the patient.
Figure 5:
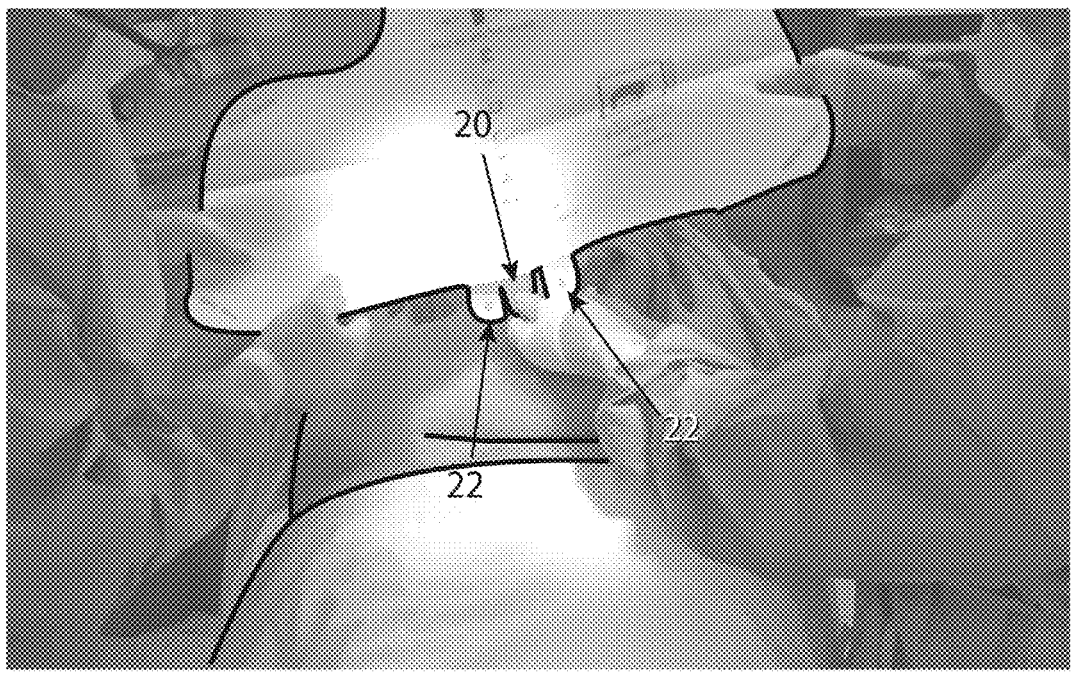
FIG. 5 is a photograph showing medical practitioners removing a first positioning panel of the release layer of the retractor/stabilizer to expose an adhesive positioning area of the top layer of the retractor/stabilizer.
Figure 6:
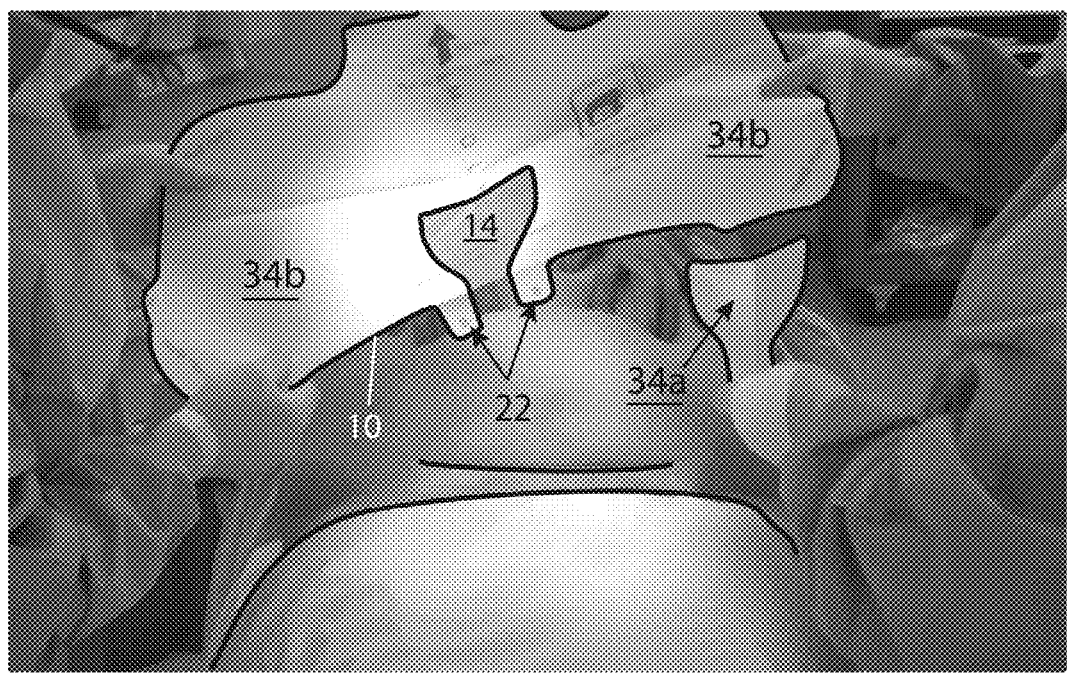
FIG. 6 is a photograph showing the retractor/stabilizer with the adhesive position area of the top layer exposed and with the medical practitioners positioning the retractor/stabilizer relative to the patient for application to the patient.
Figure 7:
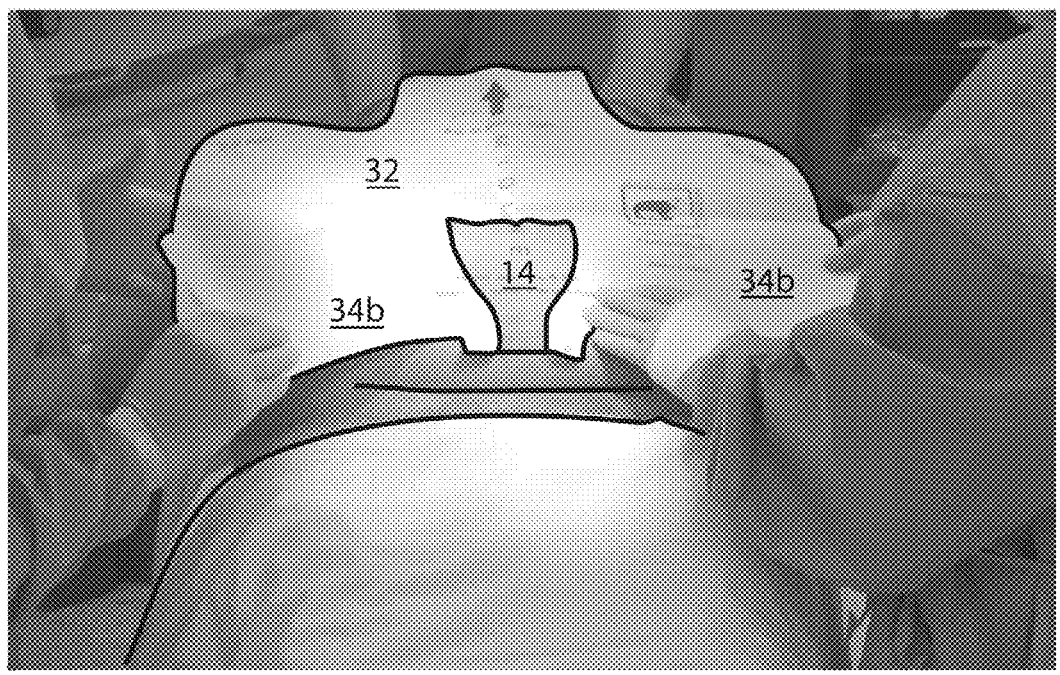
FIG. 7 is a photograph showing the retractor/stabilizer initially positioned and adhered to a lower or underside portion of the patient's panniculus (i.e., to the radius of the panniculus)

Before the retractor/stabilizer 10 is applied, medical practitioners manually retract the panniculus AP in a cephalad direction, as shown in FIG. 3. In FIG. 3, the retractor/stabilizer 10 can be seen in the lower portion of the picture. With the patient's panniculus AP (or excessive and/or redundant tissue) retracted (manually or otherwise), the bottom edge 16d of the retractor/stabilizer 10 is positioned to be between the umbilicus (or slightly above the umbilicus) and the pubic hair line, and preferably, about 2 cm to about 10 cm above the incision line I, as shown in the photograph of FIG. 4. The staff then grasps the A-tab 20, as shown in FIG. 5, and pulls downwardly to remove the center portion 34a of the lower panel 34 of the backing layer 12, as shown in FIG. 6. This exposes a window or portion of the adhesive of the top layer 14 in the area of the lower panel center portion 34a. With the center portion 34a of the lower panel 34 removed (as seen in FIG. 6), the exposed portion of the top layer is applied (via the adhesive coating A) to the panniculus, below the horizon of the panniculus (as shown in FIG. 7). At this point in the application procedure, the panniculus is still being retracted (manually or otherwise).

Figure 8:
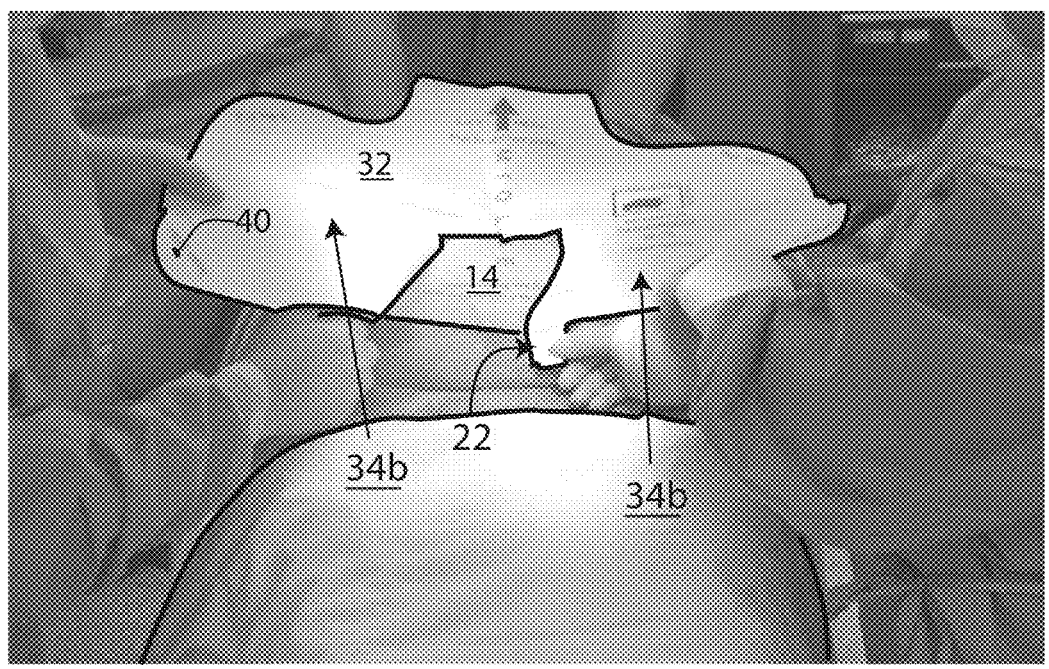
FIG. 8 is a photograph showing medical practitioners removing the remainder of the lower panel of the release layer or backing layer to expose the remainder of the top layer.
Figure 9:
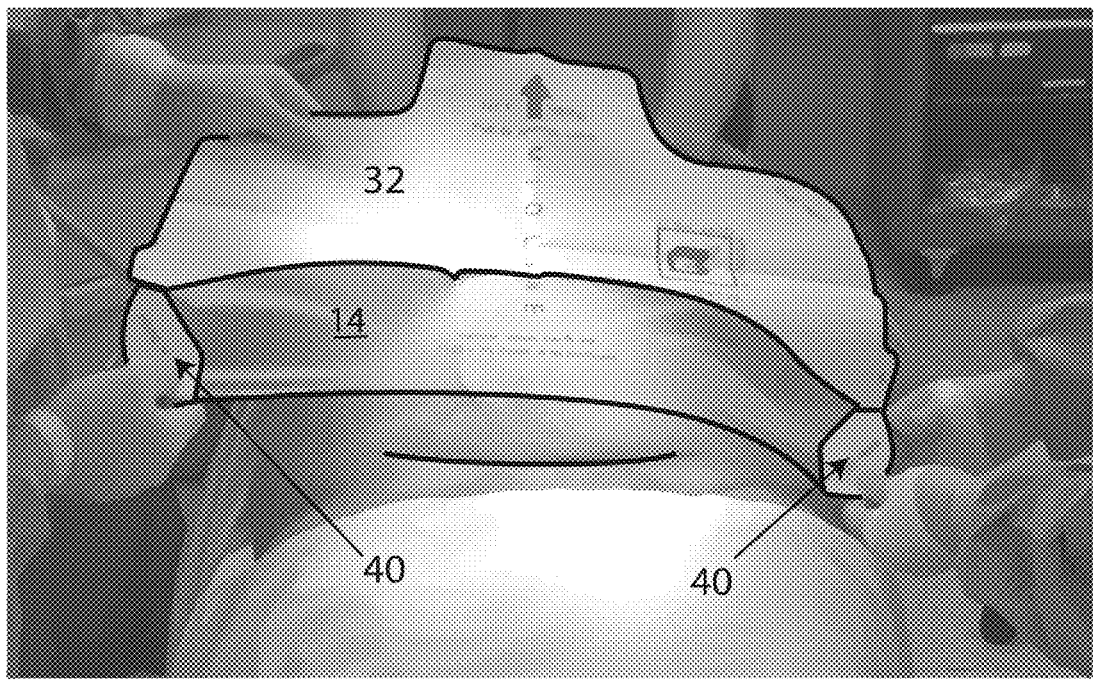
FIG. 9 is a photograph showing the lower panel of the release layer removed and the medical practitioners adhering the lower portion of the adhesive layer to the radius of the patient's abdominal panniculus.

While still retracting (manually or otherwise) the panniculus, the practitioner will pull the B-tabs 22 outwardly, as shown in FIG. 8, to remove the side portions 34b of the backing layer lower panel 34 from the top layer 14 to expose the adhesive of the remainder of the lower portion of the top layer. The two side portions 34b of the backing layer can be removed substantially at the same time or one after the other. Because the back cuts 38 define the grasping areas 40, these corner areas of the backing layer 12 remain with the top layer 14 even after the lower panel side portions 34b have been removed from the top layer, as can be seen in FIG. 9. Thus, the adhesive in the corners of the top layer remain covered, and by holding on to the top layer at these protected corner areas, the practitioner will avoid getting his/her gloves stuck to the top layer. As the lower panel side portions 34b of the backing layer are removed, the top layer 14 is held in tension (by holding the protected grasping areas 40 at the lower corners of the retractor/stabilizer and by holding the upper corners of the retractor/stabilizer and by pulling outwardly from the midline). While in this tensioned state, the lower portion of the top layer is applied to the radius of the panniculus by smoothing the top layer against the patient's skin from the midline outwardly toward the patient's hip, as shown in FIG. 9. At this point, the lower portion of the top layer 14 has been applied, attached or adhered to the radius of the panniculus. With the lower portion of the top layer 14 in position, the practitioners can stop pulling or pushing on the patient's adipose tissue and can allow the panniculus to relax and return to a natural position.

Figure 10:
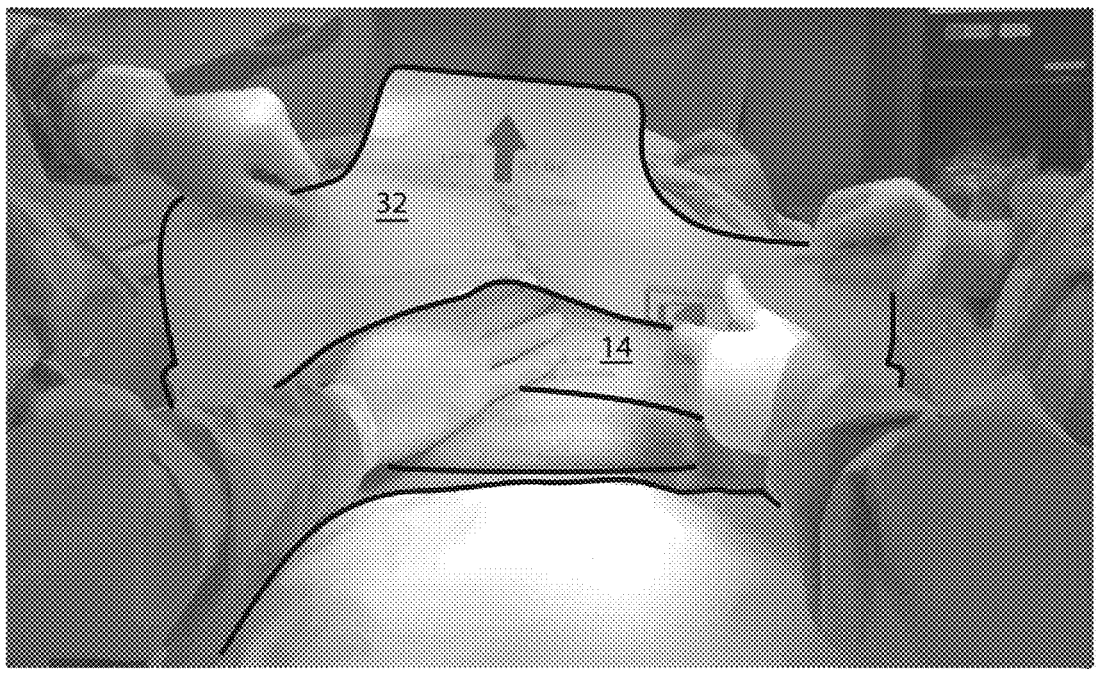
FIGS. 10 and 11 are photographs showing further steps in the application of the retractor/stabilizer in preparation for removing the upper panel of the release layer of the retractor/stabilizer.
Figure 11:
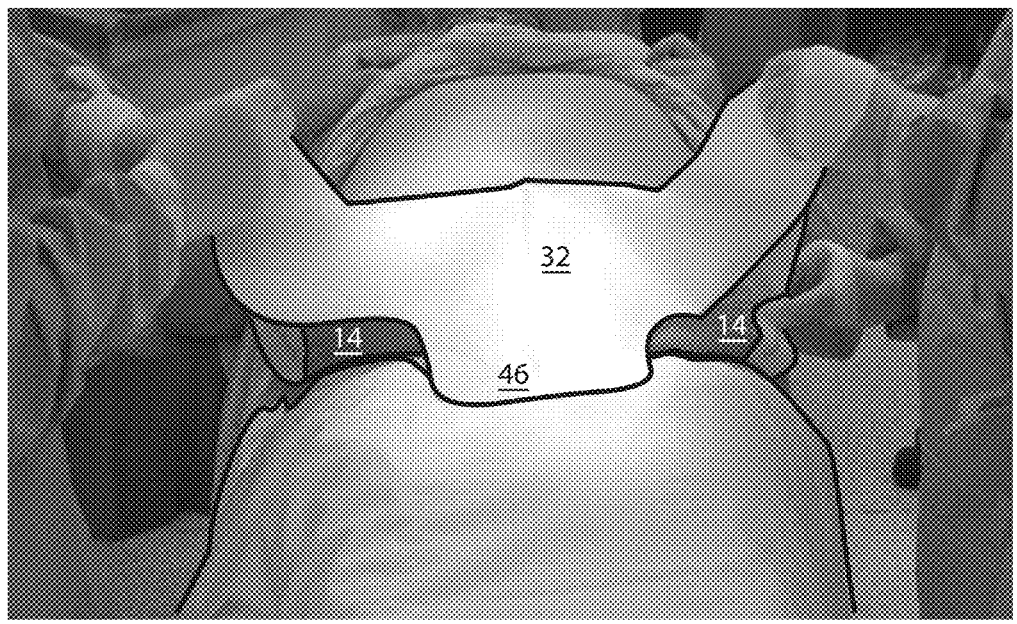
Figure 12:
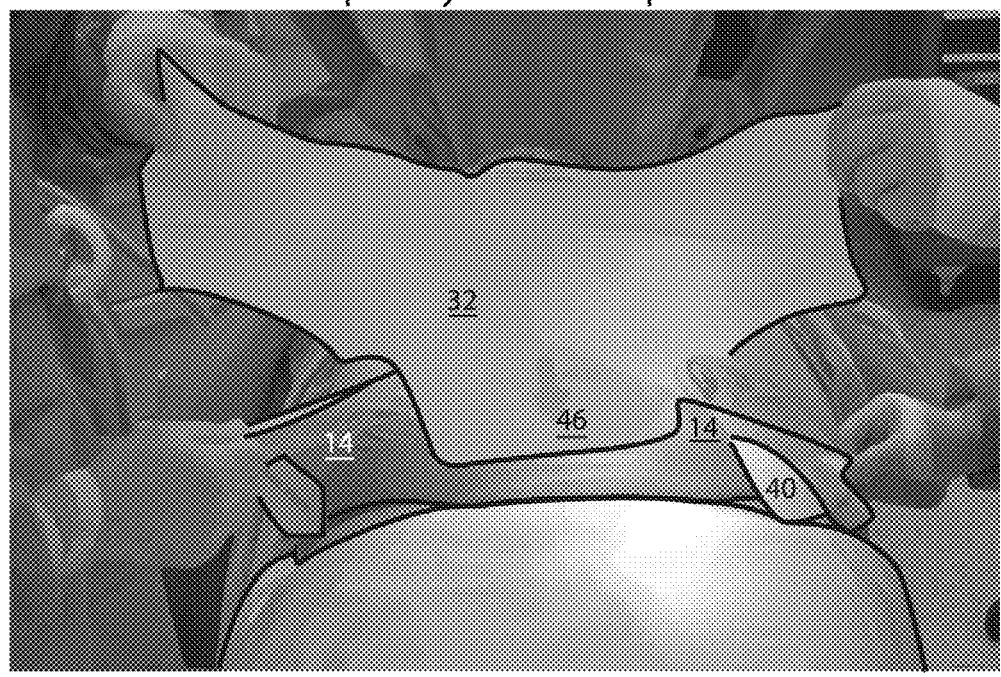
FIG. 12 is a photograph showing the medical practitioners removing the upper panel of the release layer to expose the upper area of the top layer.

Once the lower portion of the retractor/stabilizer is adhered to the radius of the panniculus (FIG. 9), the retractor/stabilizer 10 is bent or folded in a retrograde manner, so that the upper panel 32 of the backing layer generally faces upwardly, as shown in FIGS. 10 and 11. One or both of the C-tabs 24 are then grasped to pull the upper panel 32 of the backing layer 12 away from the top layer 14, as shown in FIG. 12. At this point, except for the lower and upper protected grasping areas 40 and 42, and protected neck grasping area 46, the backing panel 12 has been fully removed from the top layer. With the adhesive of the top layer exposed, the top layer should be held in tension to prevent the top layer from touching itself and folding together. The reader may have noticed that the tabs 20, 22 and 24 (FIG. 1) are labeled "A", "B", and "C", and that the A-tab 20 is used first to remove the backing layer lower center panel 34a, the B-tabs 22 are used second to remove the backing layer lower side panels 34b, and the C-tabs are used last to remove the backing layer upper panel 32. This labeling of the tabs facilitates application of the retractor/stabilizer by noting the order in which the backing layer panels are to be removed and the order in which the top layer 14 is to be applied to the patient's skin, thus producing a delivery system/process for the retractor/stabilizer.

Figure 13:
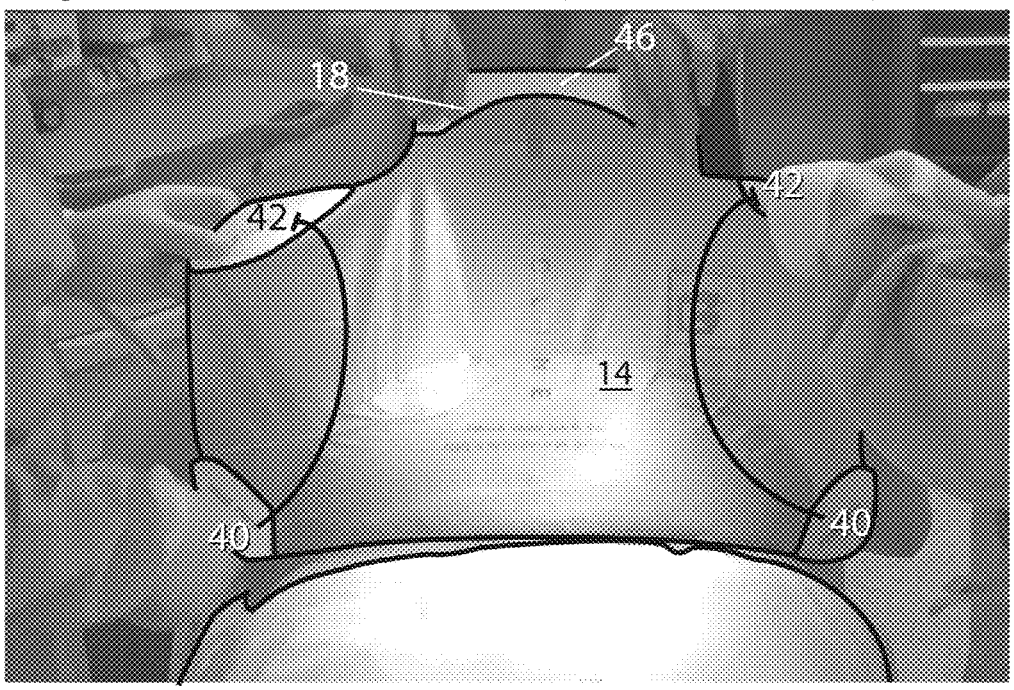
FIG. 13 is a photograph showing the medical practitioners using the grasping areas to pull the retractor/stabilizer in a cephalad direction (toward the patient's head)
Figure 14:
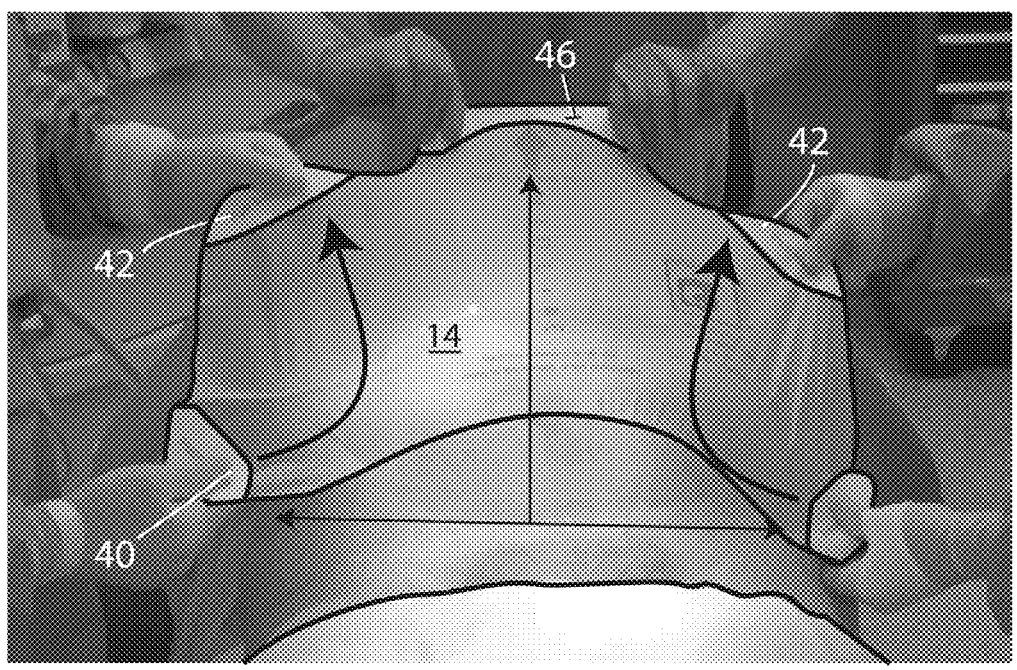
FIG. 14 is a photograph showing the medical practitioners completing the positioning and anchoring of the patient's panniculus to the patient's chest in the area of his/her xiphoid process (i.e., the lower part of the sternum) using the panniculus retractor/stabilizer.
Figure 15:
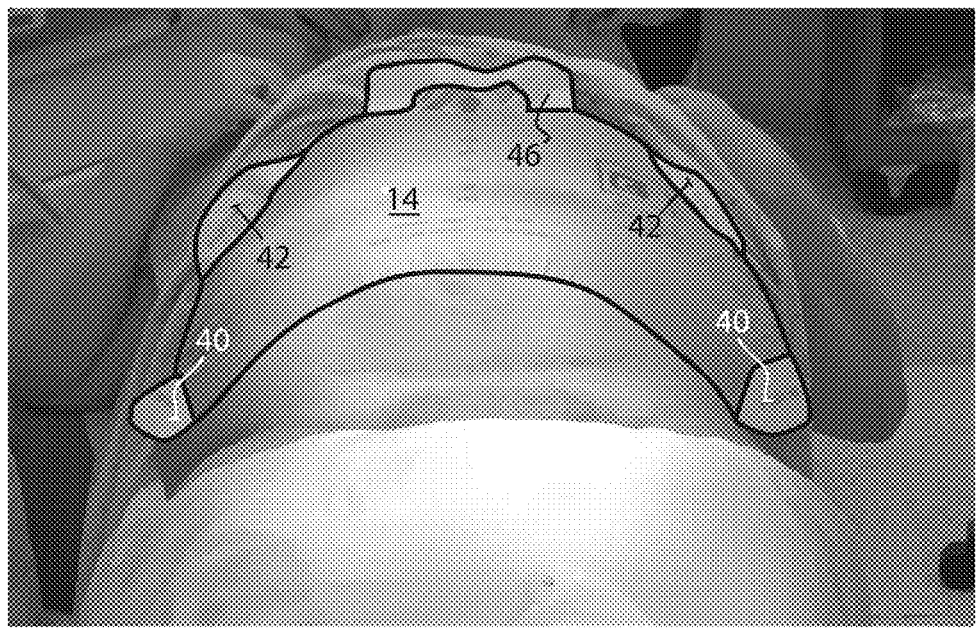
FIG. 15 is a photograph showing the retractor/stabilizer fully retracting the panniculus and applied to the patient.
Figure 16:
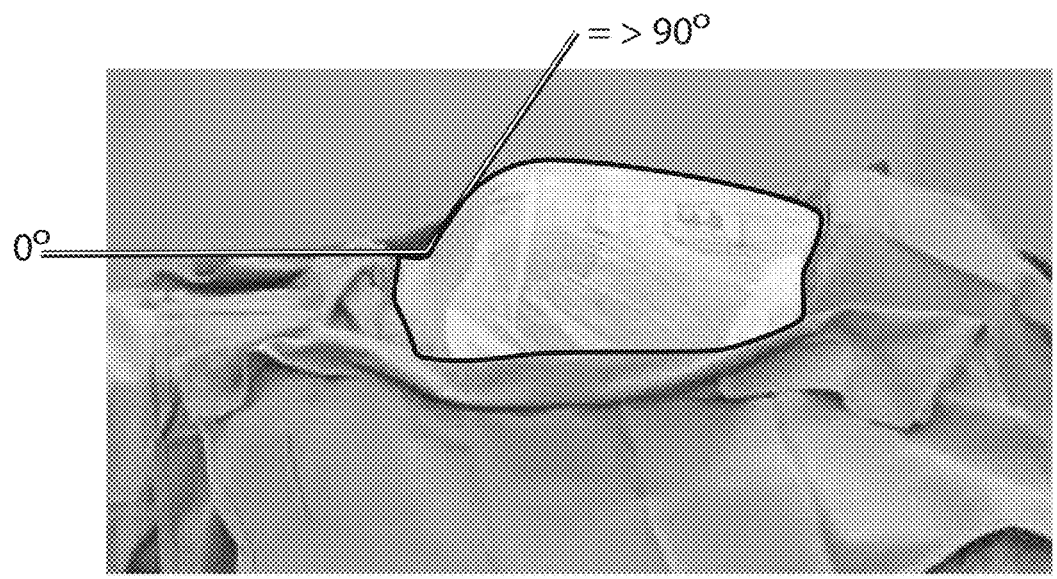
FIG. 16 is a further photograph of a patient, but from the side, showing the retractor/stabilizer applied to the patient, and demonstrating a greater than 90° retraction of the panniculus by the retractor/stabilizer to give the medical practitioner access to the targeted area.

With one technician at the head of the patient and one technician on either side of the patient, the protected tongue grasping area 46 is grasped by the technician at or near the head of the patient and the upper protected grasping areas 42 are grasped by the technicians on the opposite sides of the patient, and preferably near the shoulders. In cooperation (i.e., substantially in unison) the panniculus is retracted as follows: the person at the head of the patient pulls the protected grasping area 46 of the tongue 18 in a cephalad direction and the technician on either side of the patient pulls the top layer upwardly and toward the head holding on to the protected grasping areas 42, as shown in FIG. 13. By pulling on the top layer in this manner, the top layer is used to retract the panniculus. With the panniculus retracted, the top layer is held in tension (again, while holding on to the protected grasping areas) and smoothed over the patient's skin with the target of adhering the top of the body 16 or the tongue 18 in the area of the patient's diaphragm or sternum (i.e., in the area of the xiphoid process). This last step is shown in FIG. 14. The panniculus will now be retracted and stabilized (as seen in FIG. 15), and the abdominal exposure should be at least 90°, and can be upward of 130°. In FIG. 16, it can be seen that the abdominal exposure is greater than 90°. As long as the top layer is held in tension, should there be an error in application of the retractor/stabilizer, the retractor/stabilizer can be partially removed from the patient and reapplied. Once the retractor/stabilizer is fully adhered to the panniculus, the panniculus is allowed to relax.

With the top layer of the retractor/stabilizer 10 in place, the top layer 14 will hold the patient's panniculus in position without any further effort required by the practitioners. The shape of the retractor/stabilizer conforms to the shape of the patient and lends itself to corrugation or folding of redundant or adipose tissue which forms the panniculus. The retractor/stabilizer 10 thus effectively retracts the patient's anatomy to a more natural anatomical configuration when it redistributes and supports the excessive and/or redundant tissue (in this example, the patient's panniculus) and orients to internal anatomical landmarks. Application of the retractor/stabilizer top layer to the patient is described above by applying the top layer first to the excessive and/or redundant tissue (the panniculus) to be retracted and stabilized and then adhering the top layer to an anchor point. This could be reversed, such that the retractor/stabilizer top layer is first adhered to the anchor point, and then adhered to the excessive and/or redundant tissue to be retracted and stabilized. Thus, the retractor/stabilizer extends between the retracted and stabilized excessive and/or redundant tissue and the anchor point. In application, the retractor/stabilizer top layer can be pulled toward the anchor point (as described above in conjunction with FIGS. 3-16) after first being adhered to the excessive and/or redundant tissue, or it can be pulled away from the anchor point (after first being adhered to the anchor point).

The top layer 14 of the stabilizer/retractor is designed such that the machine direction of the top layer is generally perpendicular to the vertical axis of the stabilizer/retractor. This is shown by the arrow MD in FIG. 1. Stated differently, the machine direction of the top layer runs the width, or extends from side to side, of the retractor/stabilizer. This provides for a slightly increased yield or stretchability of the top layer in the top-to-bottom direction.

The retractor/stabilizer 10 is self-supporting and self-contained. There is no need for straps that are secured to the operating room gurney or patient examining table, and practitioners do not need to hold the panniculus in the retracted position. The only support required for the use of the device is the patient him/herself. Thus, use of the retractor/stabilizer 10 will essentially eliminate the potential for fatigue and/or injury caused to practitioners holding a patient's panniculus in place. Further, the retractor/stabilizer can be applied quickly (in less than one minute). This is substantially faster than current strap-based retractors can be applied. The fact that the retractor/stabilizer can be applied quickly and is self-supporting benefits the patient, in that the patient is likely to be less embarrassed. Further, the stabilizer/retractor when applied enables personnel to shift and lift, displace, reposition and then hold in place excessive and/or redundant tissue.

Previously, if practitioners did not use a device which included straps which adhered to the bed, they may have used tape. The use of tape (i.e., medical or even duct tape) is noisy and thus disruptive to the surgical team. Further, the tape may not be sterile, as may be required. And, the practitioners' gloves may stick to the adhesive of the tape. The retractor/stabilizer 10, which can be sterilized, eliminates these issues.

The retractor/stabilizer can be provided in different sizes (in both side-to-side width and top-to-bottom length) so that the retractor/stabilizer can be used with a Grade I panniculus (which extends to the pubic hairline) to a Grade V panniculus (which can extend beyond the patient's knees). For example, the retractor/stabilizer can have a side-to-side width of about 22" to about 26" and a length of about 17". The width of about 22" to about 26" should extend from hip to hip in most patients. The retractor/stabilizer is formed by a die cutting process, typically in the web, and, the size of the retractor/stabilizer is dictated by the capability of the equipment used to form the retractor/stabilizer. The retractor/stabilizer could be made larger (in length and/or width) using larger die cutting equipment or if made via a different process.

Figure 17:
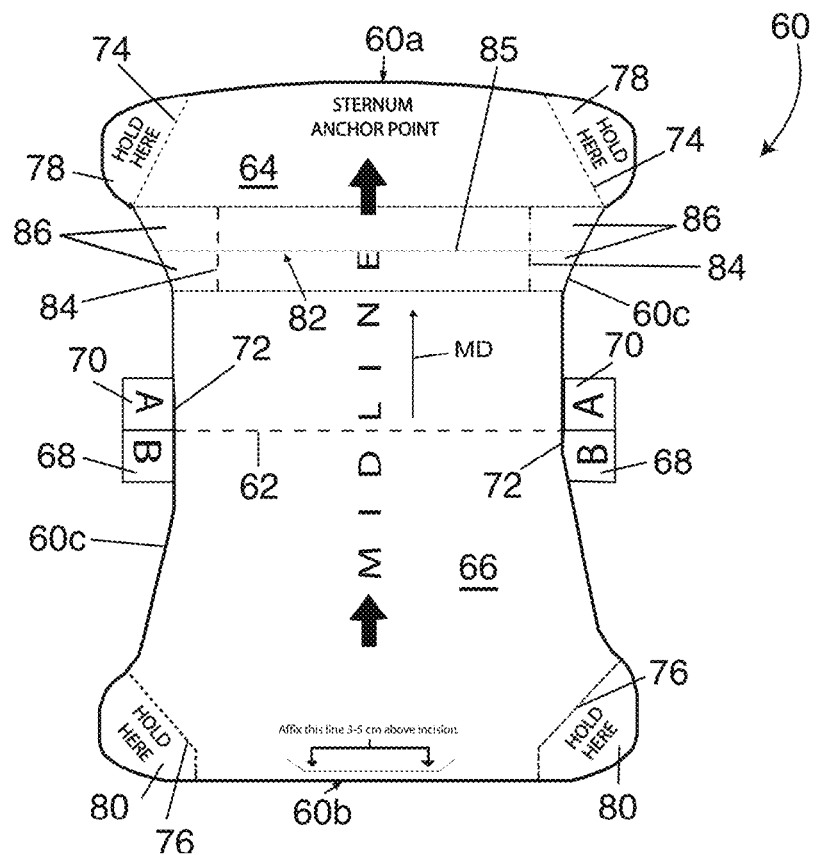
FIG. 17 is a plan view of an extension member which can be used in conjunction with the retractor/stabilizer for patients with very large BMIs.

For patients that have extremely high BMIs (i.e., greater than about 45), it may be necessary to use an extension member 60, such as shown in FIG. 17. This extension member is typically made from the same material as the retractor/stabilizer, and has a backing layer and a top layer as described above. The extension member has a top edge 60a, a bottom edge 60b and side edges 60c. The side edges 60c extend outwardly from a horizontal mid-line, and end in an enlarged (mushroom shaped) top and bottom, giving the extension member a somewhat hourglass or dog bone configuration. A back cut 62 extends across the backing layer from side-to-side at about horizontal mid-line of the extension member to divide the backing layer into an upper panel 64 and a lower panel 66. Lower panel tabs 68 (labeled "B") and upper panel tabs 70 (labeled "A") are positioned adjacent each other, extending from the sides 60c on opposite sides of the cross-cut 62. Face cuts 72 are formed in the top layer at the inner ends of the tabs 68, 70 such that pulling the tabs away from the top layer will separate the backing layer from the top layer. Although the lower edge of the upper panel tabs 70 are shown to be generally even with the cut line 72, the upper panel tabs 70 could be moved upwardly along the side edges 60c to be spaced from the lower panel tab 68. In addition, the extension member is provided with upper and lower back cuts 74, 76 at the corners of the extension member to define upper and lower protected grasping areas 78, 80 at the upper and lower corners, respectively, of the extension member.

As noted above, the retractor/stabilizer 10 is formed with the machine direction of the top layer extending in a width-wise direction. However, in the extension member, the machine direction of the top layer is generally parallel the long axis (i.e., to the midline) of the extension member, as shown by the arrow MD in FIG. 17. Thus, the extension member top layer will not have as much yield or stretchability as the retractor/stabilizer top layer.

Figure 17A:
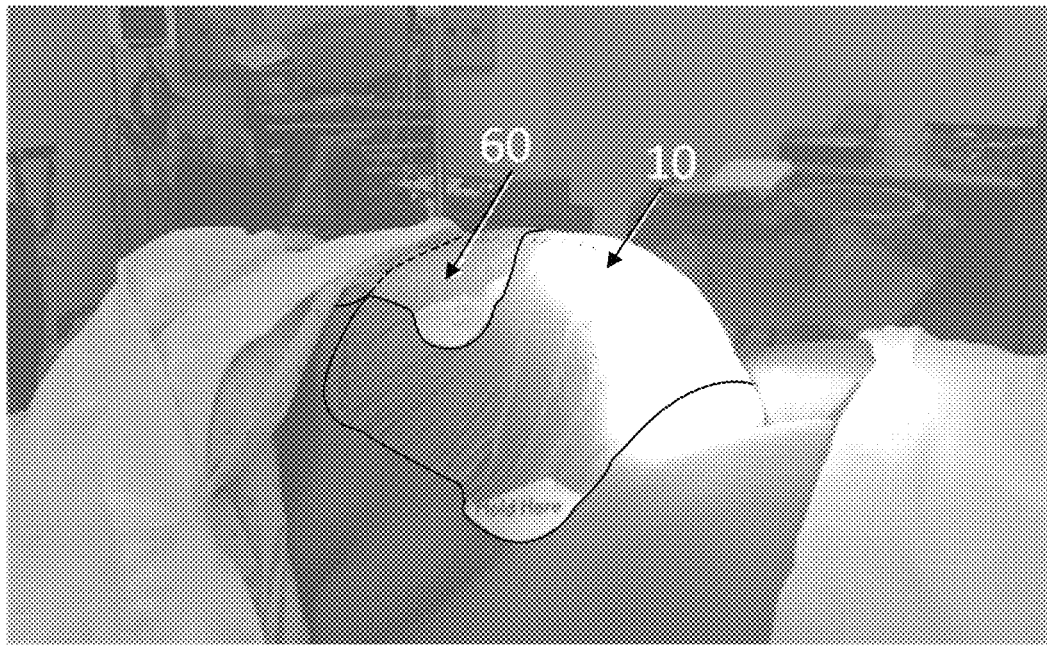
FIG. 17A is a photograph showing the use of an extension member in combination with the retractor/stabilizer to retract and stabilize the panniculus of a patient with a BMI of 77.

In use, the backing layer lower panel 66 is removed from top layer of the extension member, and while holding the extension member top layer in tension via at least the protected bottom grasping areas, the extender member is adhered to the body 16 (FIG. 1) of the retractor/stabilizer 10. The amount to which the extension member and retractor/stabilizer body overlap depends on the patient's BMI, the length of the extension member, and the amount of extension required to reach the attachment point. Thus, for example, the extension member can overlap just the tongue of the retractor/stabilizer or it can overlap a large portion of the retractor/stabilizer body. The attachment of the extension member to the retractor/stabilizer can be done before or after the backing layer upper panel 32 is removed from the retractor/stabilizer. The extension member backing layer upper panel 64 is then removed from the upper portion of the extension member 60. While holding the extension member top layer and the retractor/stabilizer top layer in tension (by grasping their respective protected grasping areas), the retractor/stabilizer-extension member assembly is pulled upwardly by grasping the upper grasp areas 78 to retract the panniculus in a cephalad direction. The assembly, comprised of the top layers of the retractor/stabilizer and the extension member, is then smoothed over, and adhered to, the patient's skin to anchor the upper end of the extension member 60 to the patient's xiphoid area. Alternatively, the upper end of the extension member could first be adhered to the patient's skin at the anchor point, and then the lower portion of the extension member could be adhered to the upper end of the retractor/stabilizer. When the retractor/stabilizer top layer is applied to the patient, the top layer is in tension between the anchor point (the xyphoid area) and the attachment point to the excessive and/or redundant tissue (the panniculus). Further, the retractor/stabilizer top layer, when applied to the patient, will apply shear forces to the patient's skin in the area of the anchor point. However, these shear forces are low and are spread out over a large area, and hence, use of the retractor/stabilizer will not adversely affect the patient. In FIG. 17D, the extension member 60' (described below in conjunction with FIG. 17B) is shown attached, secured, or adhered to the retractor/stabilizer 310 (described below in conjunction with FIG. 20).

Although it is preferred to provide the extension member as a separate part which is adhered to the retraction/stabilizer, the retraction/stabilizer can be formed to be longer, such that it effectively incorporates the extension member. FIG. 17A is a photograph showing the extension member 60 in use in conjunction with the retractor/stabilizer 10 to retract and stabilize the panniculus of a patent with a BMI of 77.

Depending on the grade or size of the patient's panniculus, a full extension member may not be needed. In fact, the full extension member may prove to be too long. Thus, the extension member can be provided with cross-perforations 82 in the top layer. Three such perforations are shown in FIG. 17. Back cuts 84 extend across the perforation lines 82 to define tabs 86 at the ends of the perforated strips. Pulling up on these tabs will remove a portion of the top layer to shorten the top layer, and thus shorten the extension member. As seen, depending on the placement of the upper protected grasping areas 78 relative to the perforated shortening lines 82, shortening the extension member may result in removing the upper protected grasping area. For this reason, the extension member may be provided with further protected grasping areas in the upper portion of the extension member. For example, further protected grasping areas could be formed about midway between the cut line 62 and the top edge of the extension member.

Figure 17B:
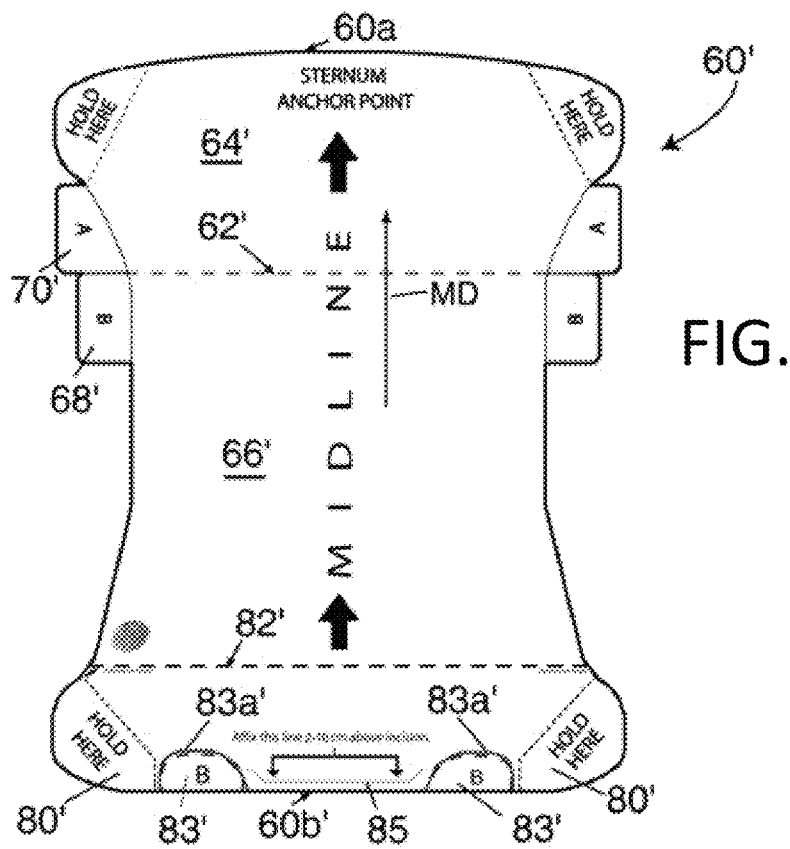
FIG. 17B is a plan view of a first alternative extension member.

An alternative extension member 60' is shown in FIG. 17B. The extension member 60' is substantially the same as the extension member 60, and thus only the differences will be discussed. In the extension member 60', the back cut 62' which divide the backing layer into upper and lower panels 64' and 66' is located closer to the top of the extension member, i.e., about ⅔ to ¾ of the length of the extension member from the bottom of the extension member. The repositioning of the back cut 62' moves the A-tabs 70' and B-tabs 68' upwardly relative to the corresponding tabs in the extension member 60. As shown, the A and B-tabs are adjacent each other, and thus are separated from each other by a through cut. The A-tab 70' extends beyond the B-tab 68'. The A-tab 70' is easily grasped because it extends beyond the B-tab 68'. When the upper panel 64' is folded retrograde along the cut line 62', the release layer 64' is removed using the A-tab 70'. Additionally, the cross-perforations or tear line 82' in the top layer used to shorten the extension member are relocated to the bottom of the extension member, and extend across the extension member just above the lower grasping areas 80'. Finally, the extension member is provided with lower tabs 83' defined by face cuts 83a in the top layer. These lower tabs extend inwardly from the lower edge 60b' of the extension member, and thus can be considered "inboard" tabs. The lower tabs 83' allow for another tab to facilitate removal of the lower panel 66' from below the tear line 82' by placing the thumb above the line and pulling across the cross-perforations. Further, in certain circumstances, the extension member can be used as the retractor/stabilizer. Thus, just above the bottom edge (and between the tabs 83'), the member 60' is provided with a guide line 85 and message that states "Affix this line 3-5 cm above incision".

Figure 17C:
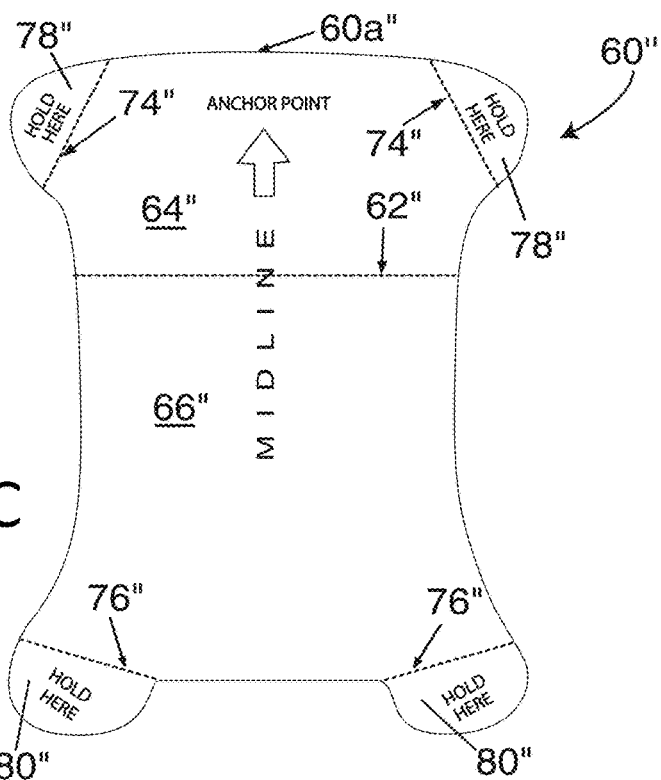
FIG. 17C is a plan view of a second alternative extension member, which is shown as being provided with a crack back, split liner or extended liner, rather than tabs, to remove the backing layer of the retractor/stabilizer from the top layer.
Figure 17D:
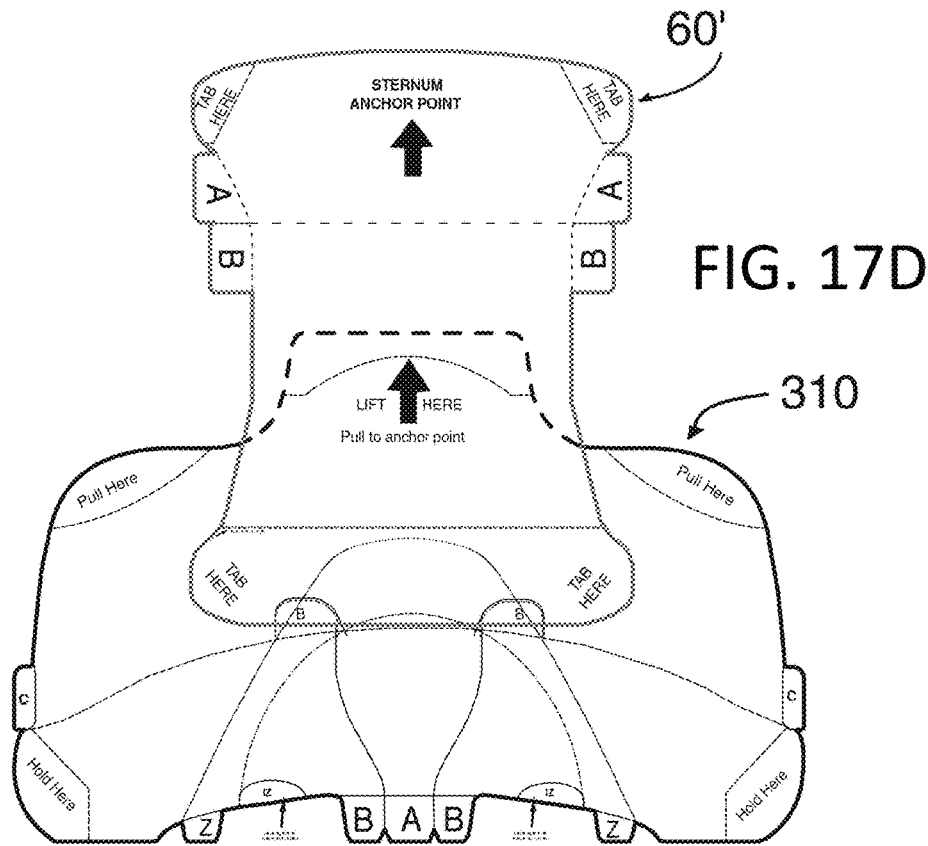
FIG. 17D is a plan view of the extension member of FIG. 17B overlapped onto, and fixed to, a retractor/stabilizer similar to that of FIG. 20.

A second alternative extension member 60" is shown in FIG. 17C. This extension member is similar to the extension members 60 and 60' of FIGS. 17 and 17B. However, it is formed without any tabs. Thus, it has upper and lower grasping areas 78" and 80" at the corners of the extension member which are formed by back cuts 74" and 76". Additionally, the member 60" includes a back cut 62" located approximately the same location as the back cut 62' of the extension member 60' to divide the backing layer into upper and lower panels 64" and 66", respectively. Because the member 60" does not include tabs, the back cut 62" is a crack back cut.

Although the extension member is described as being attached to the retractor/stabilizer to extend the reach of the retractor/stabilizer, the extension member can be used as a retractor/stabilizer by itself. That is, it need not be attached to the retractor/stabilizer body.

When the medical procedure has been completed, removal of the retractor/stabilizer 10 is simple as well. The practitioners take hold of the protected grasp areas and gently elevate the retractor/stabilizer to separate the retractor/stabilizer from the patient's skin. During removal, the patient's skin should be supported or pushed away from the retractor/stabilizer, and the removal should be accomplished in slow, short 2-3 inch segments at a time. Upon removal, the retractor/stabilizer should be disposed of in accordance with the relevant regulations. The use of the retractor/stabilizer does not lead to any residual effects to the patient. Nonetheless, the patient's skin should be assessed for any adverse reactions.

The retractor/stabilizer anchors the patient's panniculus to the patient's xiphoid area. When the practitioners release the panniculus after application of the retractor/stabilizer 10 to the patient, the panniculus relaxes slightly. Because the bottom of the retractor/stabilizer is secured to the panniculus below the horizon of the panniculus (i.e., toward the bottom of the panniculus or at the radius of the panniculus), relaxation of the panniculus will place the retractor/stabilizer top layer in tension, and it will pull against the patient's xiphoid or chest area. Thus, initially, the retractor/stabilizer is a flexible, conformable device that operates beginning in a relaxed state and uses tension to reposition, replace, and manipulate tissue, and in particular, excessive and/or redundant tissue. Upon application of the retractor/stabilizer, the underlying tissue is in compression the patient's excessive and/or redundant tissue may end up in folds or corrugations. When the panniculus is retracted, using the retractor/stabilizer, the thoracic cavity is not compressed. Rather, the tensile forces in play have been found to reduce pressure on the patient's chest (thoracic) cavity. The weight of the panniculus acts as a counterweight. The weight of the panniculus is transferred to the xyphoid area through the retractor/stabilizer, thereby, lifting the patient's diaphragm as the retractor/stabilizer pulls away from the xiphoid. With this pressure removed from the chest cavity, the anesthesiologist is provided with better access to the patient's airways, making intubation of the patient easier and making control of the patient's breathing during surgery easier. This effect has also been referred to as thoracic dilation and diaphragmatic excursion. This diaphragmatic excursion may be useful in other patients as well. For example, it may also work well during caesarian section operations, even with women who are not overweight. In these instances, the retractor/stabilizer can be secured at its lower end to the patient's abdomen. The upper end of the retractor/stabilizer can be secured to the patient's xiphoid area, in the same manner as discussed above. In this instance, the top layer would need to be made from a polymer which can be cut through, inasmuch as the retractor/stabilizer may cover the area where the incision for the caesarian section needs to be made.

If the retractor/stabilizer 10 is to be used during a surgical procedure, then the top layer is preferably formed from a fluid impervious material. Further, the top layer can be formed from a material which can be incised (i.e., cut), as noted above. The retractor/stabilizer can also be used for wound care, for example, to keep the panniculus raised to facilitate healing of an abdominal incision or other abdominal wound. In such a situation, the top layer 14 is preferably made from a breathable material through which vapor can pass. For example, the top layer could be made from a polyurethane, cloth (made from man-made or natural fibers), paper, silicone, etc. Further, although the top layer is preferably clear (i.e., transparent), it can be translucent or even opaque. Additionally, the top layer could be colored if desired.

Typically, retractors/stabilizers are used only during a medical procedure. However, because the retractor/stabilizer top layer is self-supporting, and does not attach to any external hardware (such as an operating room or examination room table), the retractor/stabilizer top layer can be left on the patient long term during healing of an incision, or to facilitate healing of a wound or infection which would otherwise be covered by redundant and/or excessive tissue (e.g., the panniculus). It is anticipated that the retractor/stabilizer can be worn as long as may be necessary for proper healing of the incision, wound or infection. In this instance, the patient would not remain in the bed, but could either be in a sitting or standing position. It is believed that in this situation, the mechanics of the retractor/stabilizer top layer would maintain the panniculus in the retracted position, to maintain the panniculus off of the incision, wound or infection, to allow healing of the incision, wound or infection. As can be appreciated, this would result in redistribution of the weight or load of the panniculus and the retractor/stabilizer would reposition the mass of redundant and/or excessive tissue of the panniculus from the lower abdominal region to more of a midline. The load of the excessive and/or redundant tissue would then be carried, at least in part, by the patient's chest (or xiphoid area) due to the anchoring of the panniculus to the chest (or xiphoid area). This redistribution of the weight of the panniculus will relieve and/or reduce the pressure and tension on the musculature and skeletal system by redistributing the weight midline. The retractor/stabilizer thus could potentially relieve pressure on the vertebrae due to the change of the center of mass to the midline. Retractors intended for such long-term use could have a top layer made from cloth, silicone or other material, as noted above, or a combination of materials, which would make the long-term application of the retractor/stabilizer more comfortable for the patient. In addition, the retractor/stabilizer top layer could be opaque, rather than transparent or translucent.

Figure 18:
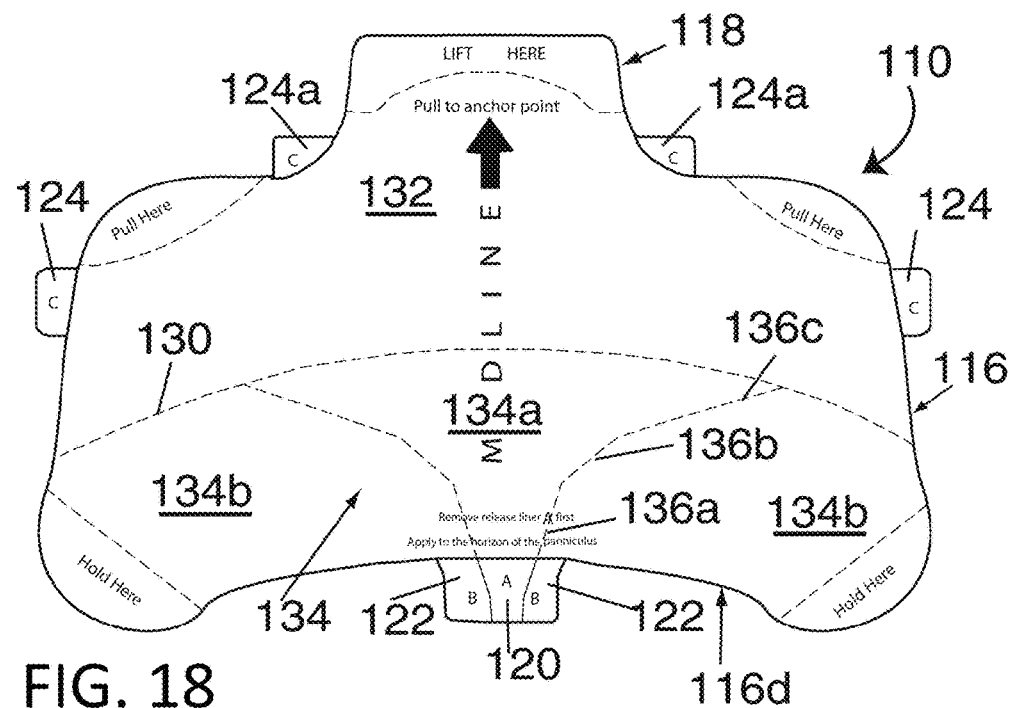
FIG. 18 is a plan view of a second embodiment of the retractor/stabilizer.

A first variation of the retractor/stabilizer is shown in FIG. 18. The retractor/stabilizer 110 shown is generally similar to the retractor/stabilizer 10 of FIG. 1. However, as can be seen, side C-tabs 124 are below the upper corners of the body 116, rather than above the lower corners of the body, and extend outwardly to a greater degree. Additionally, a second set of upper C-tabs 124a are formed at, and extend from, the junction of the body 116 with the neck 118 of the retraction/stabilizer 110. The secondary upper C-tabs 124a are associated with the backing upper panel 132 along with the side C-tabs 124. The A and B-tabs 120 and 122 are still positioned together along the bottom edge 116d of the body. However, the cuts forming the tabs are cut so that the tabs are slightly differently shaped. Further, as can be seen, the central portion 134a of the lower panel is more funnel shaped. That is, it is defined by first back cuts 136a which slope upwardly and outwardly from the top corners of the A-tab 120. Second back cuts 136b have a shallower slope and extend away from the first cuts 136a; and third back cuts 136c are shallower in slope than the cuts 136b extend from the second cuts 136b to intersect the cross-cut 130 which separates the upper panel 132 from the lower panel 134. Thus, at its top, the central portion 134a of the lower panel 134 covers about one-half of the length of the cross-cut 130. Use of the retractor/stabilizer 110 is substantially the same as the use of the retractor/stabilizer 10 (FIG. 1) as described above, and thus need not be described. However, as can be appreciated, the provision of the secondary upper C-tabs 124a provide for an additional gripping point from which the backing upper panel 132 can be removed from the top layer.

A second variation of the retractor/stabilizer 210 is shown in FIG. 19. The stabilizer 210 is generally similar to the stabilizer 10 and 110. However, there are certain notable changes. As with the retractor/stabilizers 10 and 110, the A- and B-tabs 220, 222 are generally centered along the lower edge 216d, although they are shaped slightly differently. The cuts separating the A- and B-tabs are sloped, such that the A-tab 220 is generally wedge or trapezoidal in shape. The back cuts 236 which separate the central and side portions 234a and 234b of the lower panel 234 from each other are straight and sloped. Hence, the lower panel central portion 234a of the backing is generally wedge or trapezoidal in shape.

The backing upper panel 232 has a lower edge defined by the back cut 230 which extends across the body 216 in a straight line from one side 216b to the other side 216b. The upper panel 232 includes two pair of additional back cuts 237a,b. Back cuts 237a extend inwardly from the side edges 216b above and parallel to the cut 230. The cuts 237a extend about one-third the width of the body to a point below and inward of the side edge of the tongue 218. The back cuts 237b slope upwardly from the inner end of the cuts 237a to intersect the cut ends of the arced portion 248a of the back cut 248 which defines the protected tongue grasping area 246. The back cuts 230 and 237a,b thus divide the top panel 232 into a first portion 232a which is somewhat hat shaped and two side or upper sections 232b.

As with the retractor/stabilizers 10, 110, the retractor/stabilizer 210 includes lower protected grasping areas 240 and upper protected grasping areas 242 at the lower and upper corners, respectively, of the body 216, along with the protected tongue grasp area 246. Unlike the retractor/stabilizers 10, 110, the retractor stabilizer 210 includes tabs 241 associated with the lower grasping areas and tabs 243 associated with the upper grasping areas. The neck grasping area 246 also has associated tabs 247. These tabs 241, 243 and 247 are defined by face cuts. Thus, the tabs 241, 243, and 247 allow for removal of the backing layer from the grasping areas should that be desired. Removal of the backing layer from the neck grasping area 246 may be desirable, for example, when connecting the retractor/stabilizer top layer to an extension member. This would allow for the retractor/stabilizer top layer to be laid over the top of the extension member.

The retractor/stabilizer 10 (FIG. 1) has generally outboard side tabs 24, and the retractor/stabilizer 110 (FIG. 18) has outboard side tabs 124. The retractor/stabilizer 210, on the other hand, is provided with both inboard and outboard side tabs. The retractor/stabilizer 210 has lower outboard tabs 224a which extend from the side edge of the body 216 just above the tabs 241 and inboard tabs 224b located above the outboard tabs 224a. The tabs 224a and 224b are both associated with the lower panel side portions 234b. Inboard tabs 224c, labeled with a "1" in the drawing, are associated with the first portion 232a of the upper panel, and are located at the edges of the "brim" of the hat shape of the upper panel first portion 232a. The upper panel side portions 232b are provided with inboard tabs 224d, labeled with a "2", located just above the tab 224c, and an outboard tab 224e extending from the side edge of the body 216 between the tab 224d and the upper grasp area tab 242. Additional upper tabs 224f are connected to, and extend from, the upper panel side sections 232b at the junction of the body 216 and neck 218.

In use, the retractor/stabilizer 210 would be applied substantially similarly to the retractor/stabilizer 10. The lower portion of the top layer is applied in the same manner as discussed above. However, as noted, the lower panel side portions 234b have three tabs—tabs 222, 224a and 224b—any one of which can be grasped to remove the backing lower panel side sections from the top layer. The main difference in the application of the retractor/stabilizer 210 lays in the removal of the backing layer upper panel 232. In this case, after the lower portion of the top layer has been applied to the radius of the panniculus, as described above, the upper portion is bent over, and the tabs 224c are grasped to remove the upper panel first portion 232a. While holding the top in tension by grasping at least the upper grasp areas 242, the exposed first portion 232a is then applied to the patient in the same manner as described above to initially anchor the panniculus to the xiphoid area. While still holding on to the grasping areas 242 and holding the top layer in tension, the upper panel side portions 232b are removed by pulling on any of the side inboard tab 224d, the side outboard tab 224e or the upper outboard tab 224f. The portions of the top layer that are then exposed can then be smoothed over the patient's skin to finish anchoring the stabilizer/retractor 210 to the patient's xiphoid area.

A third variation of the retractor/stabilizer is shown in FIG. 20. The retractor/stabilizer 310 is identical to the retractor/stabilizer 10. However, the retractor/stabilizer 310 is provided with a tear line 311 (defined by a perforated line) in the form of an arc which extends upwardly from the bottom edge of the retractor/stabilizer body, to define a removable panel 313 in the top layer of the retractor/stabilizer. Tabs 315 are provided for the removable top layer panel 313, and the tabs 315 are defined in part by back cuts 317 in the backing layer so that the backing layer of the tabs will stay with the top layer of the tabs when the panel 313 is removed. This will prevent the practitioners' gloves from encountering the adhesive of the top layer of the tab. Thus, pulling up on either of the tabs 315 will separate the top layer panel 313 from the lower portion of the top layer. As noted above, the machine direction of the top layer extends or runs from left to right, as shown by the arrow MD. Thus, the angle of the tear line 311 relative to the machine direction of the top layer changes due to the curvature of the tear line. To facilitate removal of the panel 313, the spacing between the perforations or cuts of the perforated line changes as the angle of the line relative to the machine direction changes. Thus, when the perforated line is parallel to the machine direction (noted by the arrow MD in FIG. 20), the spacing between the perforations of the tear line increases and the size of the perforations decreases. Additionally, as the angle defined by the perforated line and the machine direction increases, the distance between the perforations decreases and the size of the perforations increases. For example, when the tear line 311 is generally parallel to the machine direction the tear line can be defined by small dashes, micro-cuts or dots, and, as the angle defined by the perforated line and the machine direction increases, the size of these cuts can increase to the point where the perforations are essentially dashes. When the top layer is made of a material having a machine direction, the material is less resistant to tearing in the machine direction, thus the perforations are smaller and farther apart when the angle defined by the tear line and the machine direction is small. However, it is harder to tear the material when tearing against the machine direction. Thus, the perforations of the tear line 311 become longer and are closer together as the angle defined by the tear line and the machine direction increases (i.e., approaches 90°).

The removable top layer panel 313 or window can be removed, for example, when access to the patient's skin is necessary, such as during an ultrasound or other imaging procedures. In use, the top layer panel 313 is intended to be removed after removal of the backing lower panel central portion. When the panel 313 is removed, there is effectively less material adhered to the patient and thus less material that is retracting and stabilizing the excessive and/or redundant tissue. However, removal of the panel 313 does not affect the ability of the top layer to effectively function as a retractor/stabilizer.

Figure 21:
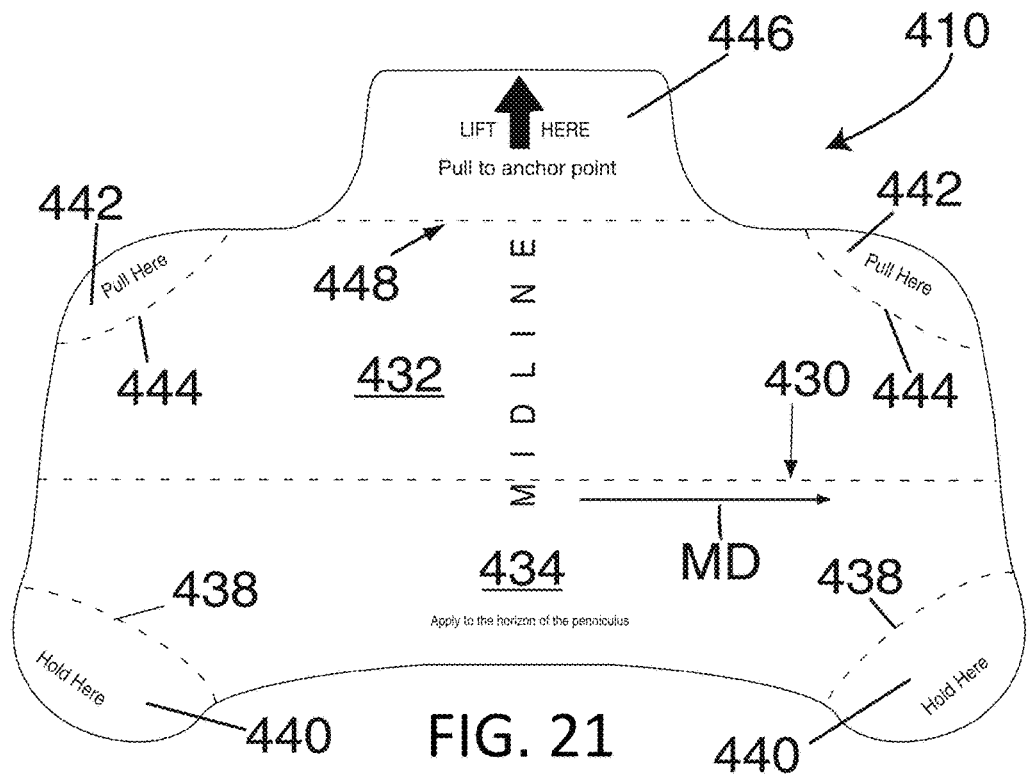
FIG. 21 is a further variation of the retractor/stabilizer in which the retractor/stabilizer is shown as being provided with a crack back, split liner or extended liner rather than tabs.

FIG. 21 shows a retractor stabilizer 410 of the same basic shape as the retractor stabilizer 10, 110, 210, and 310. The retractor/stabilizer 410 is provided with back cuts 438, 444 and 448 to define grasping areas 440, 442 and 446, respectively. It also includes a back cut 430 to divide the back panel into upper and lower portions 432 and 434, respectively. However, unlike the retractor/stabilizers 10, 110, 210 and 310, the retractor stabilizer does not have any tabs. Thus, the back cut 430 is a crack back cut, and the backing layer is separated from the top layer by folding the stabilizer/retractor to expose the edges of the panels 432 and 434 at the cut line 430.

Figure 22:
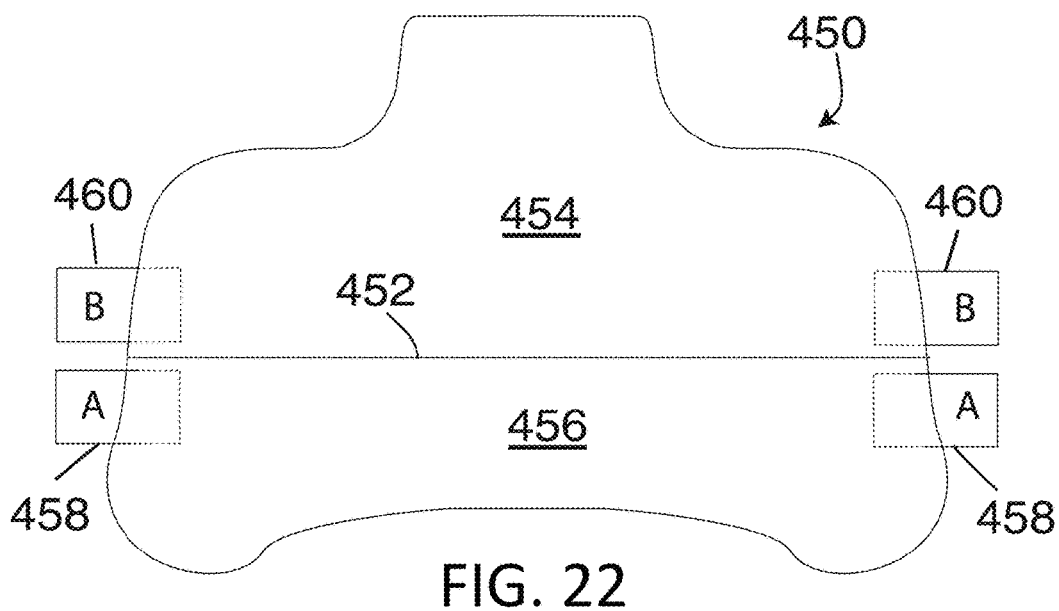
FIG. 22 is a further variation of the retractor/stabilizer in which the tabs of the retractor/stabilizer are formed separately from the body and adhered to the backing layer of the retractor/stabilizer body.

FIG. 22 shows a retractor/stabilizer 450 having a back cut 452 which divides the backing layer into an upper portion 454 and a lower portion 456. The lower portion 456 of the backing layer is provided with A-tabs 458 and the upper portion 452 of the backing layer is provided with B-tabs 460. In the retractor/stabilizers 10 (FIG. 1), 110 (FIG. 18), 210 (FIG. 19), 310 (FIG. 20), and 610 (FIG. 24) and the extensions 60 (FIG. 17), 60' (FIG. 17B), 510 (FIG. 23), 710a (FIG. 25), and 710d (FIG. 28) the tabs are formed integrally with the retractor/stabilizer body or the extension body. That is, in those embodiments, the tabs are formed as part of the die cut process that forms the respective retractor/stabilizer or the respective extension member. In the retractor/stabilizer 450, however, the tabs 458 and 460 are formed separately from the retractor/stabilizer body, and are adhered to the backing layer of the retractor/stabilizer body in a position such that when the tab is pulled away from the top layer, the back panel with which the tab is associated will be pulled away from the top layer. Although the retractor/stabilizer 450 is shown with only two backing layer panels, it will be appreciated that separately formed tabs which are then adhered to the backing layer can be provided for any of the panels of the various retractor/stabilizers or the various extension members that are disclosed herein. It will also be appreciated that the grasping areas can be formed in a similar manner. That is, a separate hand hold can be adhered to the top layer. The hand hold will have a portion extending from the retractor/stabilizer body which the technician can grasp to pull, or otherwise handle the retractor/stabilizer body when portions, or all of, the backing panel have been removed from the top layer.

We have found that the retractor/stabilizer displaces excessive and/or redundant tissues, thereby minimizing and reducing the distance between the dermis and the target area to which the retractor/stabilizer is adhered. This displacement of the excessive and/or redundant tissue greatly facilitates imaging. In obese patients, there is a layer of fatty or adipose tissue that will typically overlie the imaging target (such as an organ, joint, artery/vein, etc.). If the excessive and/or redundant tissue is not displaced, the imaging energy (i.e., ultrasound) will need to pass through the excessive and/or redundant tissue to reach the imaging target. In order to obtain a good image of the imaging target through the excessive and/or redundant tissue, the imaging power or energy, for example, of the ultrasound signal needs to be increased. When retracting and stabilizing a patient's excessive and/or redundant tissue using the retractor/stabilizer (with or without an extension member), the excessive and/or redundant tissue between the imaging target and the patient's skin is moved by the repositioning of the excessive and/or redundant tissue. This effectively reduces the distance that imaging energy (such as ultrasound energy) must travel, and thus, the need to use a higher energy power is mooted. Further, because the imaging energy travels through less tissue, the image is more defined. The reduced distance (i.e., the retraction/displacement of the excessive and/or redundant tissue) also facilitates vascular access. For example, during vascular access or nerve block procedures in the femoral region, use of an ultrasound guided needle is required to access either the femoral artery or nerve. Use of the retractor/stabilizer reduces the penetration distance required because the distance between the dermis and target site is reduced. Vascular access in the groin, for example, can be used to insert stents. Easier (or enhanced) vascular access in other regions of the body facilitates nerve block and pain management. Use of the retractor/stabilizer during radiation therapy, for example, for ovarian cancer, allows for a reduction in the amount of energy needed to treat the cancer because the distance between the skin and the target tissue is shorter. That is, less energy is required to treat the target because redundant tissue is retracted from the target area.

The retractors 10, 110, 210, 310 and 410 all work well for retracting and stabilizing a panniculus, or other excessive and/or redundant tissue. However, the size and shape of these retractors make them more difficult to use on a smaller area, such as a patient's side or when it is only desirable to move a smaller amount of excessive and/or redundant tissue. For such applications, the extension members 60, 60' and 60" could be used. These are all narrower in side-to-side dimensions.

Figure 23:
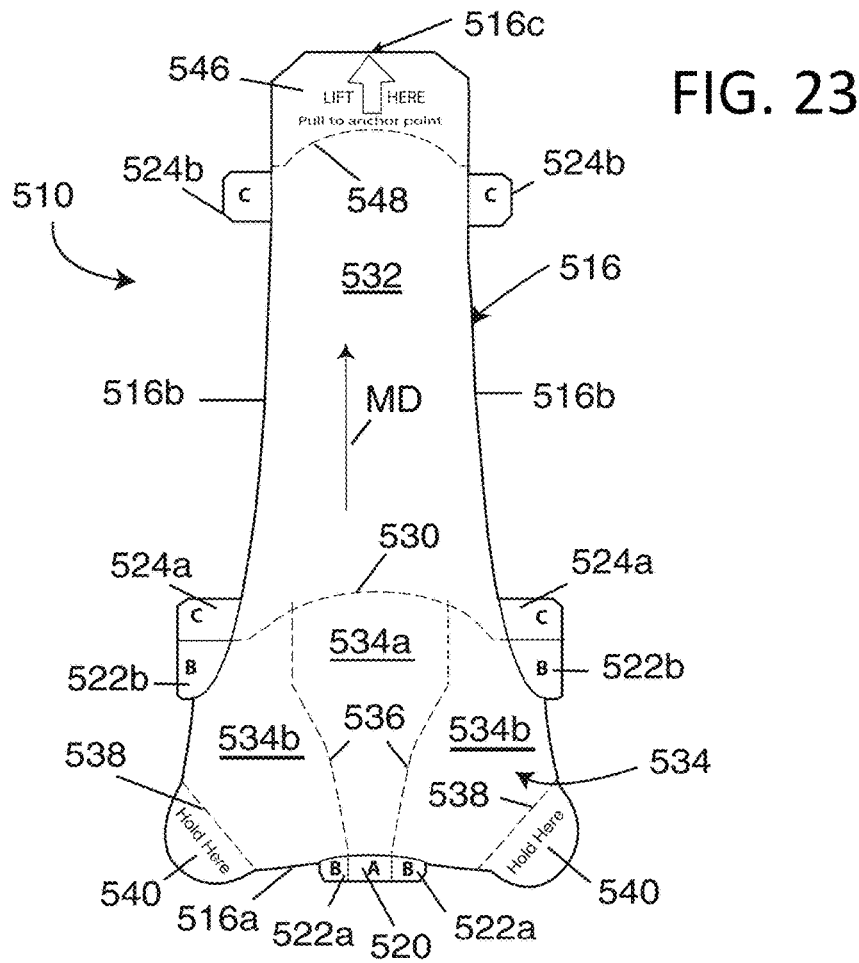
FIG. 23 is a variation of the retractor/stabilizer which can be used for procedures which do not require a large amount of adipose tissue to be repositioned, and thus may be beneficial for use on a patient's side to provide better access, for example, for imaging or vascular access.

Another narrower retractor 510 is shown in FIG. 23. The retractor 510, like the retractors disclosed above, comprises a backing layer and a top layer. Back cuts are formed in the backing layer to divide the backing layer into panels or sections and to form grasping areas. Face cuts are made in the top layer to form tabs to facilitate removal of the backing layer panels or sections. The retractor 510 includes a body 516 having a bottom edge 516a, side edges 516b and a top edge 516c. As seen, the retractor body 516 is wider at its base or bottom than at its top. For example, at its base, the retractor body 516 can have a width of about 16" (~40.5 cm) and at its top, it can have a width of about 9" (~23.9 cm). The overall length of the retractor/stabilizer 510 can be about 24" (~60.1 cm) long. The narrow top of the retractor body facilitates attachment of the top layer to a narrower or smaller area of the patient, such as the patient's side. Unlike the retractors/stabilizers 10, 110, 210, 310 and 410, in which the machine direction runs from side to side, in the retractor/stabilizer 510, the machine direction runs from bottom to top, as indicated by the arrow MD in FIG. 23.

The bottom corners of the retractor 510 are rounded and drop down relative to a middle portion of the bottom edge, giving the bottom edge 516a a slightly concave appearance. Back cuts 538 are formed in the backing layer to define lower grasping areas 540. The sides 516b slope inwardly and upwardly, and also have a slightly concave appearance. The backing layer includes a first generally upwardly arcing cut 530 which divides a lower panel 534 from an upper panel 532. A second upwardly arcing back cut 548 near the top defines the upper grasping area 546.

A pair of back cuts 536 extending between the first back cut 530 and the bottom edge 516a divide the lower panel 534 into a center portion 534a and two side portions 534b. A tab 520 at the bottom edge is associated with the center portion 534a. The side portions 534b each have a lower tab 522a which is adjacent the center portion tab 520 and upper tabs 522b which are located along the side edge 516b just below the lower dividing cut 530. The upper panel 532 similarly has lower tabs 524a and upper tabs 524b associated with it to facilitate removal of the backing layer from the upper panel. There are a set of upper and lower tabs on each side of the upper panel 532. Although, tabs could be provided on only one side if desired. The upper panel lower tabs 524*a* are located just above the lower panel tabs 522*b* and just above the dividing cut 530. The upper panel lower tabs 524*a* are separated from the lower panel tabs 522*b* by full cuts, such that the tabs 524*a* and 522*b* are independent of each other.

The upper panel upper tabs 524*b* are located just below the upper dividing cut 548. As noted above, the tabs are all defined by face cuts which allow for the top layer to remain with the backing layer to thereby facilitate removal of the backing layer from the top layer of the retractor. Conversely, the grasping areas 540 and 546 are defined by back cuts such that the backing layer stays with the top layer of the retractor when the backing layer is removed. As discussed above, this provides for an adhesive free or protected area which the practitioner can grasp without getting his/her gloves stuck to the adhesive of the top layer.

Figure 24:
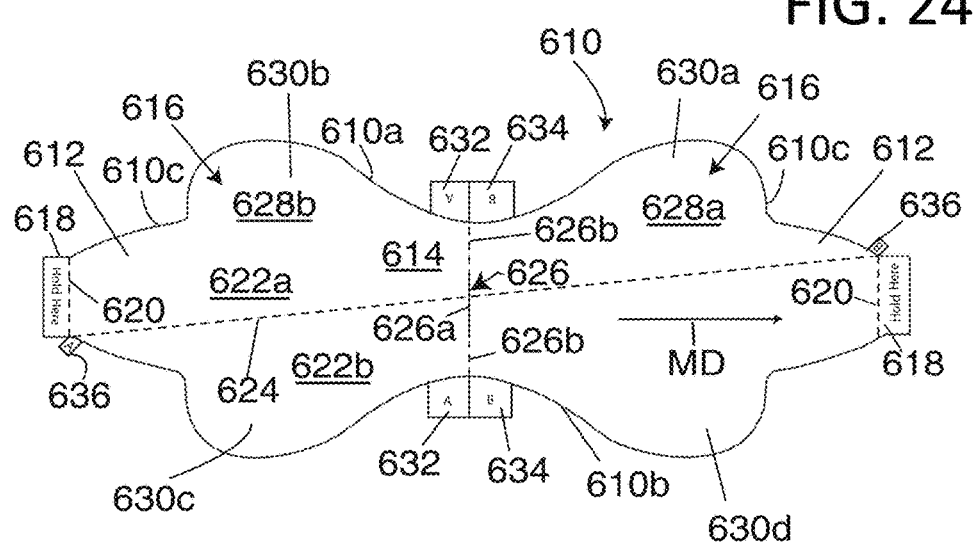
FIG. 24 shows a retractor/stabilizer which provides for two anchor points.

FIG. 24 shows another variation in the shape of the retractor/stabilizer. The retractor/stabilizer 610 is generally horizontally oriented and is substantially wider than it is tall. For example, it can be about 32" (~81.3 cm) from side-to-side and about 10" (~25.4 cm) from top-to-bottom. Due to the width of the retractor/stabilizer and the capabilities of most available die cutting machinery, the machine direction of the top layer of the retractor/stabilizer 610 runs in the side-to-side direction, as noted by the arrow MD in FIG. 24. With sufficiently large equipment, the retractor stabilizer could be formed with the machine direction of the top layer running in the top-to-bottom direction.

The stabilizer 610 is essentially dog-bone or hour-glass shaped with generally trapezoidal side extensions 612. Thus, the stabilizer has a narrow center portion 614 and widens from a waist or center portion to the wider side portions 616. The top and bottom edges 610*a,b* of the retractor/stabilizer are smooth and continuous, and define a generally concave curve which then wraps around to form curved corners which leads to the side edges 610*c*. The side extensions 612 extend from the ends of the side edges 610*c* of the side portions 616. Generally rectangular grasping areas 618 are formed at the ends of the side extensions 616 by back cuts 620 in the backing layer of the retractor/stabilizer.

The backing layer is divided into upper and lower portions 622*a,b* by a back cut 624 which extends across the stabilizer/retractor. Unlike the dividing cut of the retractor/stabilizers and extension members disclosed above, the dividing cut 624 runs on a diagonal and extends from the lower inner corner of one grasping area 618 to the upper inner corner of the opposite grasping area 618. A second dividing back cut 626 extends between the top and bottom edges at the narrowest point (or waist) of the retractor/stabilizer to divide the backing layer into left and right halves 628*a,b*. The second dividing cut 626 has a center portion 626*a* which is a full cut through the backing layer and two end portions 626*b* which are defined by perforations or micro-cuts. The two dividing cuts 624 and 626 divide the backing layer into quarters 630*a-d*, with the quarters 630*a,b* forming the upper panel 622*a*, the quarters 630*c,d* forming the lower panel 622*b*, the quarters 630*a,d* forming the right panel 628*a* and the quarters 630*b,c* forming the left panel 628*b*. Each quarter panel 630*a-d* is provided with at least one tab defined by a face cut. To this end, the retractor/stabilizer 610 has A-tabs 632 associated with the left quarter panels 630*b,c* and B-tabs 634 associated with the right quarter panels 630*a,d*. The tabs 632 and 634 are positioned at the "waist" of the retractor on opposite sides of the dividing cut 626. Additionally, secondary tabs 636 are associated with the lower left and upper right quarter panels 630*c,a*. The tabs 636 extend from the edges of the side extensions 612 adjacent the grasping areas 618. Additional secondary tabs could be provided for the other two quarter panels if desired. As noted, the secondary dividing cut 626 is, in part, perforated, with the perforations extending inwardly from the top and bottom edges of the retractor/stabilizer. This allows for the upper and lower panels to be removed from the top layer as a whole or for the backing layer to be removed from the top layer in quarters. If the upper and lower panels are to be removed as a whole, the secondary tabs 636 can be used, and it may not be necessary to use the A and B-tabs 632 and 634. If the backing layer is to be removed in quarters, then most likely, the practitioner will use the tabs 632 and 634 to remove the quarter panels 630*a-d*. The dividing cut 624 forms an angle (other than 90°) with the dividing cut 626. However, the dividing cut could be generally perpendicular to the dividing cut 626, if desired.

The larger width of the retractor/stabilizer 610, as compared to the stabilizers 10, 210, 310, 410, and 510, allows for the retractor/stabilizer 610 to be used with large BMI patients. The lower half of the side portions 616 of the retractor/stabilizer effectively define two areas where the top layer can be adhered to the patient, and the upper half of the side portions 616 of the retractor/stabilizer effectively define two areas where the top layer can be anchored to the patient. Thus, the retractor/stabilizer effectively defines two spaced apart points of attachment to the excessive and/or redundant tissue to the retracted/stabilized/repositioned and two spaced apart anchor points. In addition, the retractor/stabilizer 610 could be used for retracting both breasts of patient.

Figure 25:
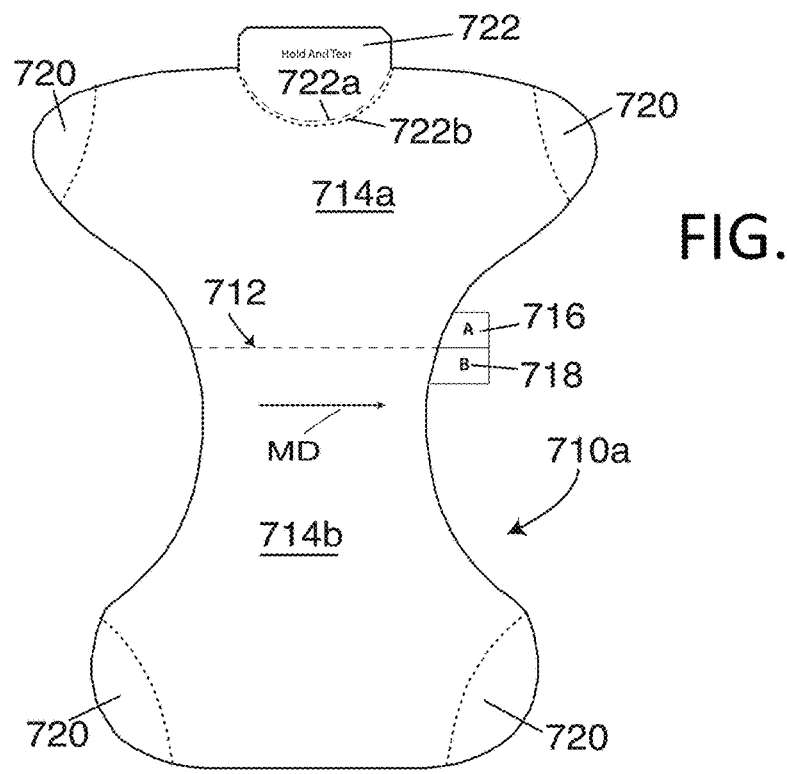
FIG. 25 is a basic retractor/stabilizer with a shape different from the shape of the retractor/stabilizer of FIG. 1.
Figure 26:
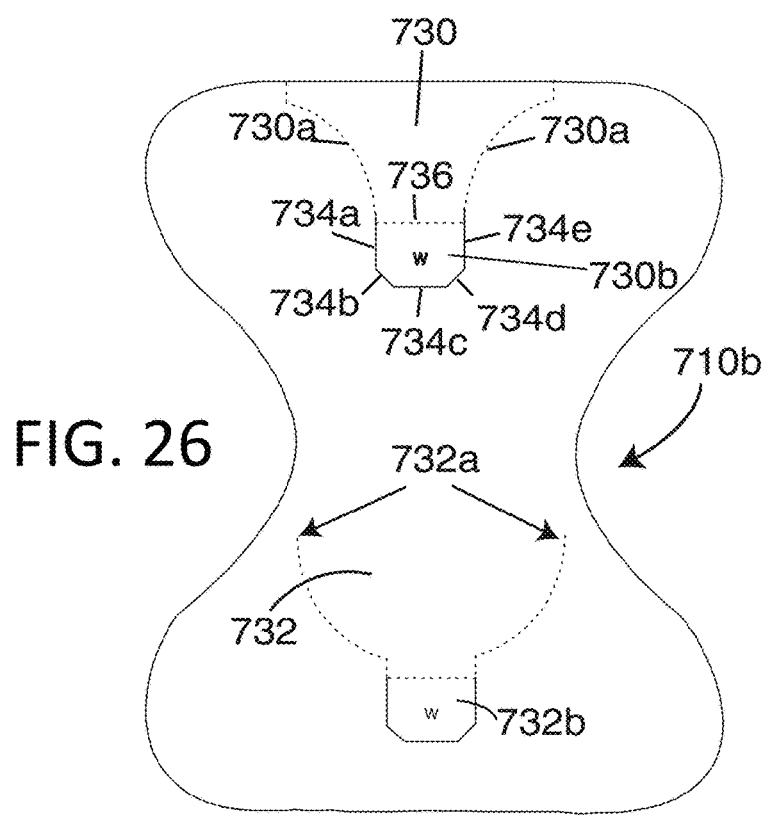
FIGS. 26-28 show various modifications that can be made to the retractor/stabilizer of FIG. 25.
Figure 27:
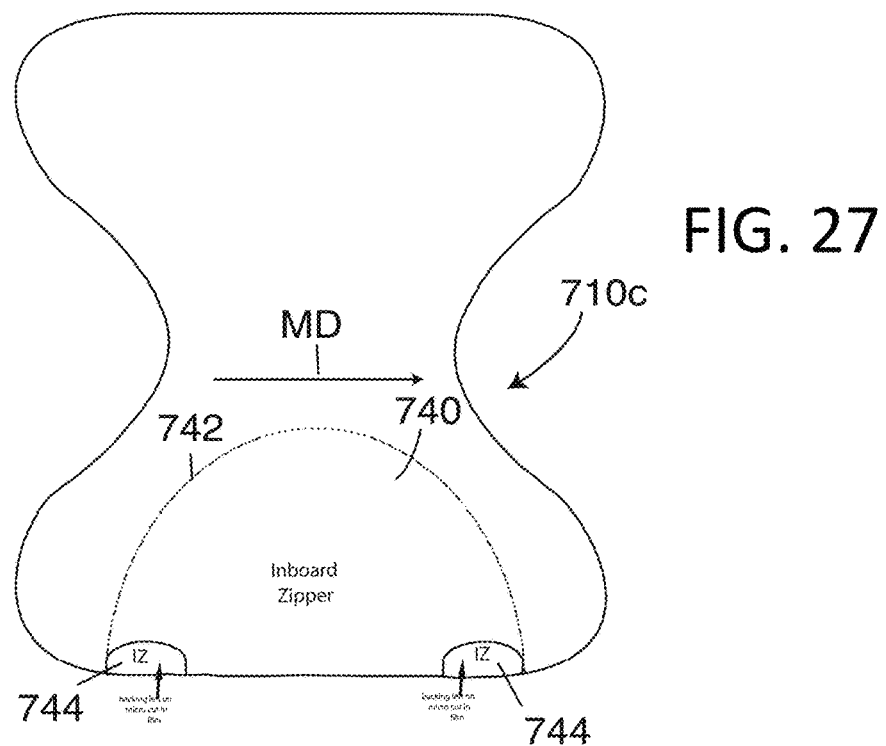

FIGS. 25-28 show variations for a vertically oriented, generally dog-bone or hour glass shaped retractor/stabilizer. Thus, the machine direction for the top layer of these retractor/stabilizers runs cross-wise, as shown by the arrow MD in FIG. 25. The retractors/stabilizers of FIGS. 25-28 are all generally symmetrical about a vertical center line (with reference to the drawings). In the retractor/stabilizers of FIGS. 25 and 28, the top portion of the retractor/stabilizer is wider than the bottom portion. Thus, these two retractor/stabilizers are not symmetrical about a horizontal center line. On the other hand, the top and bottom portions of the retractor/stabilizers of FIGS. 26 and 27 are approximately the same size, and thus, these two retractor/stabilizers are symmetrical about a horizontal center line. The retractors/stabilizers of FIGS. 25-28 show different variations. It will be appreciated that variations of the retractors/stabilizers can be used together. That is, for example, the features of the retractor of FIG. 25 can be added to the retractor of FIG. 26, and vice versa.

Retractor/Stabilizer of FIG. 25

The retractor/stabilizer 710*a* (FIG. 25) may be considered a basic retractor stabilizer. It is provided with dividing cut 712 which divides the backing layer into an upper panel 714*a* and a lower panel 714*b*. The dividing cut is positioned above the vertical center of the retractor/stabilizer, and thus the lower panel 714*b* is larger than the upper panel 714*a*. An A-tab 716 is associated with the backing layer upper panel 714*a* and a B-tab 718 is associated with the backing layer lower panel 714*b*. The tabs 716 and 718 both extend from a side edge of the retractor/stabilizer, and are positioned adjacent each other with the dividing cut between the two tabs being co-linear with the dividing back cut 712 in the backing layer. Of course, the dividing cut between the tabs 716 and 718 is a full cut which extends through both the top layer and bottom layer, so that the two tabs will be independent of each other. Although the tabs 716, 718 are next to each other, they could be spaced apart from each other along one side of the retractor/stabilizer, or they could be formed on opposite sides of the retractor stabilizer. Additionally, A and B-tabs could be formed on both sides of the retractor stabilizer.

Grasping areas 720 are formed at the corners of the retractor/stabilizer and are defined by back cuts in the backing layer, such that the backing layer of the grasping area is separate from the backing layer upper and lower panels. A top grasping area 722 is formed at the top of the retractor/stabilizer, and is defined by a generally rectangular extension from the top edge of the retractor/stabilizer. This top grasping area 722 is formed in part by a back cut 722*b* which is generally concave. Additionally, a perforated line 722*a* is formed in the top layer. The perforated line 722*a* is also concave and is shaped complimentarily to the back cut 722*b*. Lines 722*a* and 722*b* are spaced offset and not directly over each other so that 722*a* has a smaller radius than 722*b*. The provision of the perforated line 722*a* in the top layer and the back cut 722*b* in the backing layer allows for the grasping area 722 to be separated or removed from the rest of the retractor/stabilizer 710*a* should that be desired.

Retractor/Stabilizer of FIG. 26

In FIG. 26, a retractor/stabilizer 710*b* is provided with an upper window 730 and a lower window 732. The upper window 730 is defined by perforated lines 730*a* formed in the top layer of the retractor/stabilizer and which extend from the upper edge inwardly to a tab 730*b*. The tab 730*b* is defined by through cuts 734*a-e* which define the bottom and side edges of the tab 730*b* and extend through both the top layer and backing layer of the retractor/stabilizer. A further back cut 736 defines a top edge of the tab 730*b*. The through cuts 734*a-e* separate the sides and bottom of the tab 730*a* from both the top layer and the bottom layer without separating the tab itself from the top layer in the area of the window. The back cut 736 which defines the top edge of the tab separates the backing layer of the tab from the rest of the backing layer. Thus, when the backing layer is removed from the top layer, the backing area in the tab 730*b* will remain with the top layer of the tab. As noted the cuts defining the window 730 are defined by perforations which extend from the upper edge of the retractor/stabilizer. Thus, the window 730 is opened by pulling upwardly on the tab 730*b* to separate the top layer in the area of the window from the rest of the top layer of the retractor/stabilizer. Because the backing layer remains with the tab 730*b*, the window 730 can be "opened" (that is, the window panel 730 can be lifted) after the retractor has been adhered to the patient. The lower window 732 is formed substantially identically to the upper window 730, and is defined by a pair of tear lines 732*a* in the top layer which extend from opposite sides of the window's tab 732*b*. However, the window 732 is fully in the interior of the top layer of the retractor/stabilizer. That is, no portion of the window 732 is at an edge of the retractor/stabilizer. Further, the ends of the perforated tear lines 732*a* are not joined. Thus, the material of the top layer between the ends of the tear line 732*a* effectively define a hinge for the window, thereby allowing for the window 732 to be closed after it has been opened. The windows 730,732 can be used to remove the top layer to facilitate imaging such as ultrasound imaging where direct contact of the imaging head with the dermis is necessary. The perforated lines which define the bottom window are radiused, such that the bottom window 732 is generally semi-circular in shape. The upper window 730, on the other hand, narrows from the top edge of the retractor/stabilizer to the tab along generally concave lines. Thus, the upper window 730 is generally horn-shaped.

Retractor/Stabilizer of FIG. 27

FIG. 27 shows a retractor/stabilizer 710*c* with a semicircular removable top layer panel 740 at the bottom of the retractor/stabilizer. This removable panel 740 is substantially similar to the removable panel 313 of the retractor/stabilizer 310 (FIG. 20). The removable panel 740 is defined by a semi-circular tear line 742 in the top layer. Inasmuch as the angle of a tangent 742 with the machine direction MD varies along the perforated line, the sizes of the perforations vary along the line 742, as discussed above. Thus, when the perforated line is parallel to the machine direction (noted by the arrow MD in FIG. 27), the spacing between the perforations increases and, as the angle defined by the perforated line and the machine direction decreases, the distance between the perforations decreases (approaching and going away from the top of the arc). Additionally, the size of the perforations increase as the angle defined by the perforated line and the machine direction increases (i.e., approaches 90°). For example, when the tear line 742 is generally parallel to the machine direction the tear line can be defined by dots (or micro-cuts) and, as the angle defined by the tear line and the machine direction increases, the size of these cuts can increase. This change in the size and separation of the perforations is shown in FIG. 20. The retractor/stabilizer 710*c* includes inboard tabs 744 at the bottom edge of the retractor/stabilizer and at opposite sides of the removable panel 740. The inboard tabs 744 are defined by back cuts in the backing layer such that the backing layer remains with the top layer of the tab when the backing layer is removed from the top layer.

Figure 28:
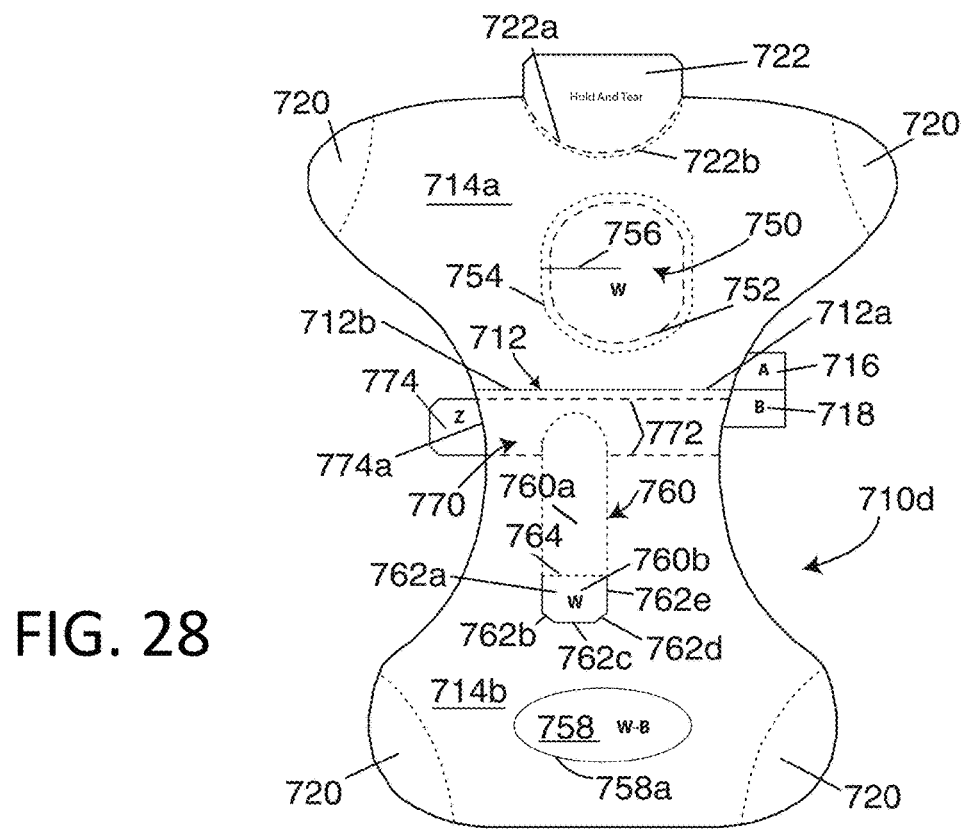

Retractor/Stabilizer of FIG. 28

FIG. 28 shows a retractor/stabilizer 710*d* which includes variations of the features noted in the retractor/stabilizers 710*a-c* (FIGS. 25-27). The retractor/stabilizer 710*d* is provided with a dividing back cut 712 which divides the backing layer into an upper panel 714*a* and a lower panel 714*b*. The dividing back cut is positioned above the vertical center of the retractor/stabilizer, and thus the lower panel 714*b* is larger than the upper panel 714*a*. An A-tab 716 is associated with the backing layer upper panel 714*a* and a B-tab 718 is associated with the backing layer lower panel 714*b*. The tabs 716 and 718 both extend from a side edge of the retractor/stabilizer, and are positioned adjacent each other with the dividing full cut between the two tabs being co-linear with the dividing back cut 712 in the backing layer. The dividing back cut 712 includes a first perforated portion 712*a* which extends inwardly from the edge of the backing layer from which the tabs 716 and 718 extend, and a second portion 712*b* which extends from the end of the first portion 712*a* to the opposite edge of the backing layer. Because the cut 712 is, in part, perforated, it is not fully divided into two separate portions. Thus, the backing layer can be removed from the top layer as a single piece (by not tearing along the perforated portion 712*a* of the dividing cut 712) or in two pieces (by tearing along the perforated portion 712*a* of the dividing cut 712).

Grasping areas 720 are formed at the corners of the retractor/stabilizer 710*d*. Additionally, a top grasping area 722 is formed at the top of the retractor/stabilizer, and is defined by a generally rectangular extension from the top edge of the retractor stabilizer. This top grasping area 722 is formed in part by a back cut 722*b* which is generally concave. Additionally, a perforated line 722*a* is formed in the top layer. The perforated line 722*a* is also concave and is shaped complimentarily to the back cut 722*b*. The provision of the perforated line 722a in the top layer and the cut line 722b in the backing layer allows for the grasp area 722 to be separated from the rest of the retractor/stabilizer 710a should that be desired. Lines 722a and 722b are spaced offset and not directly over each other so that 722a has a smaller radius than 722b. The provision of the perforated line 722a in the top layer and the cut line 722b in the backing layer allows for the hold/tear out area 722 to be separated from the rest of the retractor/stabilizer 710a, should that be desired.

The top portion of the retractor stabilizer is provided with an optional window 750. A back cut 754, which is shown to be generally oval, is formed in the backing layer. In addition, a perforated tear line 752 in the top layer (defined by a perforated face cut) is surrounded by the backing layer cut 754 and is shaped generally complementarily to the backing layer cut 754. A full cut 756 (which extends through both the top layer and the backing layer) extends from the perforated face cut 752 into the window 750. In view of the back cut 754, the backing layer within the window 750 will remain with the top layer when the backing layer is removed from the top layer, and the area of the window will not be adhered to the patient. The full cut 756 enables the practitioner to extend a finger, for example, through the full cut 756 to reach under the backing layer in the area of the window, even after the top layer has been adhered to a patient. The practitioner can then simply tear the top layer along the perforated face cut 752 to separate the top layer in the window 750 from the rest of the top layer. This will expose the patient's skin in the area of the window to allow, for example, an incision or puncture not through the top layer or for imaging.

A second window 758 is formed in the lower portion of the top layer by a face cut 758a. Thus, the top layer in the area of the window 758 will separate from the rest of the top layer and remain with the backing layer when the backing layer is separated from the top layer. Thus, the window 758 will automatically be "opened" when the backing layer is removed.

An elongate extending window 760 extends generally axially through the narrow portion of the retractor/stabilizer 710d. The window 760 is formed substantially similarly to the windows 730 and 732 of FIG. 27. The window 760 is thus defined by a perforated tear line 760a extending from a tab 760b. The tab 760b is formed identically to the tab 730b of the retractor/stabilizer 710c (FIG. 27) and is defined by through cuts 762a-e and a cut 764 in the backing layer. The perforated tear line 760a defines an elongate strip having a rounded end. That is, the ends of the tear lines extending from the tab 760b are joined. Thus, when the tab 760b is lifted and pulled, the top layer in the window/panel 760 is fully removed. Thus, the window 760 is not a reclosable window, as is the window 732 of the retractor/stabilizer 710c. The window 760 demonstrates, in part, that the internal removable window/panel can be formed in any desired shape.

Lastly, the retractor/stabilizer 710d includes a tear strip 770 which extends across the width of the retractor/stabilizer and is operable to remove the top portion of the top layer from the bottom portion of the top layer to enable the practitioner to shorten the overall length of the top layer that is applied to the patient. The tear strip 770 is defined by two generally parallel perforated face cuts or tear lines 772 which effectively extend across the width of the retractor/stabilizer top layer. In the illustrative embodiment of FIG. 28, the window/panel 760 extends into the tear strip 770, and thus, the window/panel 760 interrupts the lower of the two tear lines 772. A tab 774 (labeled "Z" in FIG. 28) extends from an edge of the retractor/stabilizer 710d between the two tear lines 772. The tab 774 is defined in part by a back cut 774a in the backing layer such that the backing layer will remain with the top layer of the tab when the backing layer is separated from the top layer of the retractor/stabilizer, and so that the tab 774 will remain with the tear strip 770 upon separation of the backing layer from the top layer. Should the practitioner decide to shorten the top layer, all that is necessary is to grasp the tab 774 and to pull it across the stabilizer top layer. The tear strip 770 can be removed (to shorten the top layer) either before or after the backing layer has been separated from the top layer. As shown, the tear strip 770 is positioned below the dividing cut 712, but could be positioned elsewhere on the retractor/stabilizer. Additional tear strips could also be provided to allow the top layer to be shortened to one of a selected number of lengths. As can be seen from the retractor/stabilizer 710d, the size, shape, and position of windows and tear strips can be changes as desired.

Benefits of Use

The use of the retractor/stabilizer is discussed above in repositioning and stabilizing the panniculus of a patient for abdominal access during surgeries or procedures which require access to the abdomen or groin. Additionally, the increased access to the patient's airways (thoracic dilation and diaphragmatic excursion) is noted above.

It has also been determined that when the retractor/stabilizer is utilized to retract, stabilize and reposition excessive and/or redundant tissue, additional tissue in the vicinity of the repositioned excessive and/or redundant tissue is also repositioned, and resulting in a reorientation of the surgical planes in the patient. Thus, for example, use of the retractor/stabilizer on a 340 lb. (~154 kg) patient may move the additional tissue to reorient the surgical planes of the patient such that the patient's surgical planes are more similar to the surgical planes of a 140 lb. (~63.5 kg) patient. This repositioning of this additional tissue reduces the distance between the patient's skin and targets beneath the skin. As noted above, this facilitates procedures such as imaging and radiation treatment. Current imaging (i.e., ultrasound, sonogram, etc.) techniques require that the excessive and/or redundant tissue above the imaging target be compressed and that a higher energy level be used than with patients having a normal body mass index. Currently, in radiation treatment, the power of the energy source must be increased to have sufficient energy at the target. The repositioning of this additional adipose tissue substantially eliminates the need for practitioners to compress the patient's flesh in the area to be imaged, and for both imaging and radiation treatment, the need for higher energy is reduced. Similarly, the repositioning of the additional adipose tissue facilitates vascular access (such as in the groin area), because it should be easier for the practitioner to locate an artery (such as the femoral artery) or vein, and the practitioner may not need to push the needle through as much excessive and/or redundant tissue. For the same reasons, the repositioning of excessive and/or redundant tissue due to the retraction and stabilization of excessive and/or redundant tissue also aids in application of nerve blocks. Again, for the same reasons, even abdominal access is made easier because the amount of additional excessive and/or redundant tissue that the practitioner must cut through is reduced. For example, in a C-section, the distance from the incision to the uterus is reduced.

Although the retractor/stabilizer is shown in the Figures for retracting and stabilizing a patient's panniculus, it can be used to retract and stabilize excessive and/or redundant tissue on any portion of the body, including breasts, hips, back, buttocks, thigh, etc. The overall shape of the retractor/stabilizer may need to be modified slightly from the shapes shown in the figures for use in some of these areas. For example, a narrower retractor/stabilizer (such as the retractor 510 of FIG. 23) may prove easier to use on a patient's side or to retract and stabilize a breast. Further, as can be appreciated, the anchor point will vary depending on the location of the excessive and/or redundant tissue to be retracted and stabilized. For example, if the excessive and/or redundant tissue is at the hip, it may be desirable to use the patient's back and/or abdomen as anchor points.

Although described generally with only one anchor point (in addition to the attachment to the excessive and/or redundant tissue), the retractor/stabilize can use multiple anchor points, i.e., the extender at the xiphoid lengthens or extends the anchor point used to retract the panniculus during a C-section of an extremely high BMI patient. The addition of a supplemental device, such as the extension member, produces an anchor point at which the primary retractor/stabilizer can be anchored. This anchor point can be an additional anchor point, and, in fact, can be two or more additional anchor points. For example, the extender can enable anchoring of the breast to the side or shoulder; or of the hip to the side of the chest; of the neck to the sternum; etc. Further, if more than one anchor point is used, the retractor/stabilizer can incorporate a "bridge" between the anchor points. That is, top layer material can be stretched (i.e., held in tension) between the two anchor points).

As can be appreciated from the above, the retractor/stabilizer can be quickly adhered to a patient. Affixing the stabilizer/retractor (actually affixing the top layer of the retractor/stabilizer) to a site with little or no adipose (such as the center of the back, the sternum, the groin, the bottom of a foot, etc.) creates an anchor point on the patient that is remote from the excessive and/or redundant tissue to which the retractor/stabilizer retracts. The retractor/stabilizer is more efficient and more secure than devices currently available. Further, when the retractor/stabilizer has been adhered to a patient, the retractor/stabilizer orients the patient's anatomy to a natural position and reorients the surgical plane.

From the forgoing, it can be seen that the retractor/stabilizer can be used for numerous types of procedures, including, but not limited to, trauma care, imaging, mapping, electrode placement, monitoring, radiation therapy, cardiac catheterization, fetal ultrasound or sonography, laparotomies (C-sections, total abdominal hysterectomies, hernias, bowel resections, etc.), incision and wound care, vascular access, nerve block and similar techniques used during anesthesiology, orthopedic and neurological procedures (such as spinal access, joint replacement, etc.), and plastic surgery (i.e., breast tissue management).

As can be appreciated, the various retractor/stabilizers and extension members disclosed provide for a device which can be quickly and easily deployed and applied to retract and then stabilize the excessive and/or redundant tissue of a patient. The use of the back cuts and face cuts which define the various tabs enable practitioners to easily remove the backing layer from the top layer without having to come into contact with the adhesive of the top layer. Additionally, the protected grasping areas allow the practitioners to manipulate the top layer, even after the backing layer has been removed to expose the adhesive, without contacting the adhesive. This substantially reduces the possibility of the practitioners' gloves from becoming stuck to the adhesive layer of the top layer. Further, as discussed, the retractor/stabilizer can be used during a medical procedure (i.e., surgery or examination) or can be used to facilitate healing of an incision, wound or infection on the patient that would otherwise be covered by excessive and/or redundant tissue.

In a broad sense, what is provided is an adhesive device, which in the preferred embodiment is formed from a single two-ply material which has a top layer and a backing layer. The device includes a body portion in which either a section of the top portion is removed from the patient after it has been applied, or the bottom portion (as in the windows) is removed from the top portion or the bottom portion is removed from the top portion (as in the backing layer panels). In either case, there is a tab portion associated with the removable portion. Inasmuch as the device is formed from a single sheet of two-ply material, both the body portion and the tab portion have an upper layer and a backing layer. The tab is associated with the removable portion, and is defined in part, by a cut in the other layer. Thus, for example, the in the A, B and C tabs 22, 22, and 24 (FIG. 1), the backing layer of the tab portion remains associated with the backing layer of the body portion, and a cut is formed in the top layer to separate the tab portion top layer from the body portion top layer. Conversely with the Z-tabs 315 which remove the window panel (FIG. 20), the tab portion top layer remains associated with the body portion top layer, and a cut in the backing layer separates the tab portion backing layer from the body portion backing layer.

Although the device has been described for use as a retractor/stabilizer, the tab design can have applications in other devices. For example, the tab design could be used in wound dressing bandages, labels, or other multi-layer applications.

As various changes could be made in the above constructions without departing from the scope of the invention, it is intended that all matter contained in the above description or shown in the accompanying drawings shall be interpreted as illustrative and not in a limiting sense. The area of the top layer 14 exposed with the lower panel central portion removed serves as a locating or positioning portion of the top layer. Although a centrally located positioning portion is preferred, the positioning portion could be located toward one of the sides of the lower panel 34. This would result in the backing lower panel having two, instead of three, portions. The various tabs could be relocated, as can the protected grasping areas. Several overall shapes for retractor/stabilizers have been disclosed. However, the retractor/stabilizer is not limited to the disclosed shapes, and can be formed in any desired size and shape. What is important is that the retractor/stabilizer be sized and shaped such that it can support the excessive and/or redundant tissue that is to be repositioned by the retractor/stabilizer. Additionally, as noted briefly above, the retractor can have 2 or more anchor points. These variations are illustrative only.

The invention claimed is:

1. A method for retracting and stabilizing excessive and/or redundant tissue or for compressing redundant tissue, the method comprising adhering a one-piece retractor-stabilizer to a patient; the retractor-stabilizer comprising a tension member having a lower surface, a backing layer, and an adhesive covering substantially the entire lower surface of the tension member to removably adhere the backing layer to the lower surface of the tension member; the method comprising:

removing said backing layer from said tension member to expose said adhesive on the lower surface of the tension member;

adhering a first portion of the tension member directly to redundant and/or excessive tissue of the patient;

pulling the tension member to place it in tension, and then adhering a second portion of the tension member directly to at least one anchor point on the patient; said second portion being spaced from said first portion and said at least one anchor point being spaced from said redundant and/or excessive tissue;

whereby the step of pulling the tension member and then adhering the second portion of the tension member directly to the patient results in the area of the tension member between the first portion and the second portion being adhered directly to the patient between the redundant and/or excessive tissue and the anchor point while in a tensioned state, such that substantially the entire lower surface of the tension member is adhered directly to the patient in a tensioned state, and whereby the excessive or redundant tissue loads against the first and second portions of the tension member thereby placing substantially the entire tension member in tension.

2. The method of claim 1 wherein the tension member is self-supporting and self-contained, and is secured only to the patient.

3. The method of claim 1 wherein the excessive and/or redundant tissue is a panniculus; the step of adhering the first portion of the tension member to the excessive and/or redundant tissue encasing the radius of the panniculus.

4. The method of claim 1 wherein the tension member conforms to the shape of the patient upon application of the tension member to the patient and supports the excessive and/or redundant tissue after application.

5. The method of claim 1 wherein said tension member defines a top layer of said retractor-stabilizer; the retractor-stabilizer further including:

at least one protective grasping area located at an edge or corner of said top layer, said grasping area comprising a portion of said top layer and a portion of said backing layer, whereby said backing layer of said grasping area remains with the top layer of said grasping area during the step of removing the backing layer from the tension member; such that said grasping area defines a substantially adhesive free surface for said tension member when the backing layer is removed from the top layer; and at least one tab associated with the backing layer and independent of said grasping area; such that pulling on the tab in a direction away from the top layer will remove the backing layer from the top layer;

said step of removing said backing layer from said top layer comprising holding onto said grasping area, grabbing the at least one tab and pulling the at least one tab away from the top layer to remove the backing layer from the top layer to expose the adhesive of the top layer at substantially all portions of said top layer, but without exposing adhesive in the grasping portion of said top layer;

said step of adhering a first portion of said tension member to the patient comprising adhering a lower portion of the top layer directly to the excessive and/or redundant tissue; and said step of adhering a second portion of the tension member while in tension to the patient comprising adhering an upper end of the top layer directly to said at least one anchor point on the patient.

6. The method of claim 5 wherein the top layer is secured first to the excessive and/or redundant tissue; said method comprising pulling the top layer towards the at least one anchor point after the first portion of the top layer has been adhered to the excessive and/or redundant tissue and then securing the upper end of the top layer to the at least one anchor point.

7. The method of claim 5 wherein the top layer is secured first to the at least one anchor point; said method comprising pulling the top layer towards the excessive and/or redundant tissue after the top layer has been adhered to the at least one anchor point and then securing the lower end of the top layer to the excessive and/or redundant tissue.

8. The method of claim 5 wherein the excessive and/or redundant tissue is located at a hip area of the patient, and the at least one anchor point is a front and/or back of the patient.

9. The method of claim 5 wherein the excessive and/or redundant tissue is located on a back of the patient; and said anchor point is spaced axially from said excessive and/or redundant tissue.

10. The method of claim 5 wherein the excessive and/or redundant tissue is breast tissue; and said anchor point is a shoulder or side area of said patient.

11. The method of claim 5 wherein the excessive and/or redundant tissue is a panniculus, and the anchor point is a xiphoid area of the patient.

12. The method of claim 5 comprising:

a step of manually or otherwise retracting the excessive and/or redundant tissue prior to adhering the lower portion of the top layer to a radius of the excessive and/or redundant tissue; and allowing the excessive and/or redundant tissue to relax after the lower portion of the top layer has been adhered to the radius of the excessive and/or redundant tissue;

pulling the top layer toward the at least one anchor point, and then, carrying out the step of adhering the upper end of the top layer to said at least one anchor point.

13. The method of claim 1 wherein the backing layer is divided into an upper panel and a lower panel, the stabilizer-retractor comprising a tab associated with each panel;

said step of removing the backing layer from said tension member comprising a step of removing the lower panel of the backing layer to expose the adhesive in a lower portion of the top layer; and a step of removing the upper panel of the backing layer to expose the adhesive in an upper portion of the top layer; said step of removing the upper panel of the backing layer from the tension member being performed after the step of adhering the first portion of the tension member to the redundant and/or excessive tissue.

14. The method of claim 13 wherein said lower panel of said backing layer is divided in to a positioning portion and at least one second portion; said step of removing the lower panel of the backing layer comprising;

removing the positioning portion of said backing layer from the top layer to expose a positioning portion in the lower portion of the top layer, adhering the positioning portion of the lower portion of the top layer to the excessive and/or redundant tissue;

removing a remainder of the lower portion of the backing layer to expose the adhesive in the remainder of the lower portion of the top layer (except for in the grasping areas); and adhering the remainder of the lower portion of the top layer to the excessive and/or redundant tissue.

15. The method of claim 1 wherein the retractor-stabilizer remains on the patient after completion of a medical procedure to maintain the excessive and/or redundant tissue in a retracted position, to relieve pressure, and maintain the excessive and/or redundant tissue off of an incision, wound or infection to facilitate healing of the incision, a wound, or an infection which would otherwise be covered by the patient's excessive and/or redundant tissue.

16. The method of claim 1, wherein the method for retracting/stabilizing excessive and/or redundant tissue facilitates a medical procedure.

17. The method of claim 16 wherein the medical procedure improves and/or does not restrict diaphragmatic excursion, the at least one anchor point being at a xiphoid area of the patient; the method comprising anchoring the excessive and/or redundant tissue of the patient to the xiphoid area of the patient, and, once the excessive and/or redundant tissue is anchored, allowing the excessive and/or redundant tissue to relax; wherein the excessive and/or redundant tissue is an abdomen of a pregnant woman undergoing a caesarian section operation or a panniculus of an obese person.

18. The method of claim 16 wherein said medical procedure is an imaging procedure; said method further comprising removing a predefined panel from the top layer to expose the patient's dermis.

19. The method of claim 18 wherein said predefined panel is removed after said top layer has been adhered to the patient.

20. The method of claim 16 wherein said medical procedure requires vascular access in a groin area of the patient.

21. The method of claim 16 wherein said medical procedure comprises mapping, electrode placement, monitoring, fetal ultrasound, ultrasound guided needle procedures, or sonography, laparotomies, incision/wound care, vascular access, access for nerve block used during anesthesiology, radiology/oncology, orthopedic and neurological procedures, plastic surgery, ENT procedures, and/or trauma.

22. A method of claim 1 wherein said method reduces a distance through tissue to a target site in the patient to reduce the distance surgical tools and/or imaging energy must pass to reach the target site.

23. A method for preventing chest wall compression and diaphragm restriction during a surgical procedure, comprising adhering a tension member to the patient; the tension member comprising a single sheet of material having a lower surface substantially completely coated with an adhesive which will adhere to the dermis of a patient and a backing layer covering said adhesive; said step of adhering the tension member to the patient comprising:
 removing said backing layer from said tension member to expose said adhesive;
 adhering a first portion of the tension member directly to the patient in an area proximate the patient's diaphragm;
 stretching the tension member in a desired direction to place the tension member under tension;
 adhering a second portion of the tension member directly to the patient in an area proximate the patient's xiphoid process and upper chest wall while the tension member is tensioned, said second portion being spaced from said first portion; and
 adhering a third portion of the tension member which is remote from the first and second portions directly to the patient in the patient's abdominal region such that the third portion is adhered to redundant and/or excessive tissue of the patient on or about the abdominal region
 whereby the steps of adhering the first, second, and third portions of the tension member directly to the patient results in the area of the tension member between the first, second, and third portions being adhered directly to the patient, such that substantially the entire lower surface of the tension member is adhered directly to the patient, and whereby the excessive or redundant tissue loads against the first and second portions of the tension member thereby placing the tension member in tension.

24. A method for retracting and stabilizing excessive and/or redundant tissue or for compressing redundant tissue, the method comprising adhering a one-piece retractor-stabilizer to a patient; the retractor-stabilizer consisting of a tension member having a lower surface, a backing layer, and an adhesive covering substantially the entire lower surface of the tension member to removably adhere the backing layer to the lower surface of the tension member; the retractor-stabilizer defining at least one grasping area and at least one tab associated with the backing layer; the method comprising:
 removing said backing layer from said tension member by pulling on said at least one tab to expose said adhesive on the lower surface of the tension member; said grasping area being formed such that the backing layer in the grasping area remains with the tension member in the grasping area to define an adhesive free zone of the tension member after the backing layer has been removed from the tension member;
 adhering a first portion of the tension member directly to redundant and/or excessive tissue of the patient; and pulling the tension member in the desired direction to place it in tension,
 adhering a second portion of the tension member directly to at least one anchor point on the patient while the tension member is in tension; said second portion being spaced from said first portion and said at least one anchor point being spaced from said redundant and/or excessive tissue;
 whereby the step of adhering the second portion of the tension member directly to the patient results in the area of the tension member between the first portion and the second portion being adhered directly to the patient between the redundant and/or excessive tissue and the anchor point, such that substantially the entire lower surface of the tension member is adhered directly to the patient, and whereby the excessive or redundant tissue pulls against the second portion of the tension member thereby placing the tension member in tension.

* * * * *